United States Patent [19]

Dusza et al.

[11] Patent Number: 4,521,422

[45] Date of Patent: Jun. 4, 1985

[54] ARYL AND HETEROARYL[7-(ARYL AND HETEROARYL)PYRAZOLO[1,5-a]PYRIMIDIN-3-YL]METHANONES

[75] Inventors: John P. Dusza, Nanuet, N.Y.; Andrew S. Tomcufcik, Old Tappan, N.J.; Jay D. Albright, Nanuet, N.Y.

[73] Assignee: American Cyanamid Company, Stamford, Conn.

[21] Appl. No.: 612,812

[22] Filed: May 24, 1984

Related U.S. Application Data

[63] Continuation-in-part of Ser. No. 506,966, Jun. 23, 1983, abandoned.

[51] Int. Cl.$^3$ ............... C07D 487/04; A61K 31/505
[52] U.S. Cl. .................................. 514/258; 544/281; 514/906
[58] Field of Search .................. 544/281; 424/251

[56] References Cited

U.S. PATENT DOCUMENTS 4,178,449 12/1979 Dusza et al. ............... 544/281
4,236,005 11/1980 Dusza et al. ............... 544/281
4,281,000 7/1981 Dusza et al. ............... 544/281

Primary Examiner—Donald G. Daus
Assistant Examiner—S. A. Gibson
Attorney, Agent, or Firm—Anne M. Rosenblum

[57] ABSTRACT

Aryl and heteroaryl[7-(aryl and heteroaryl)pyrazolo[1,5-a]pyrimidin-3-yl]methanones which are new compounds active as anxiolytic, anticonvulsant, sedative-hypnotic and skeletal muscle relaxant agents in mammals and the novel process of making these compounds.

31 Claims, No Drawings

ARYL AND HETEROARYL[7-(ARYL AND HETEROARYL)PYRAZOLO[1,5-a]PYRIMIDIN-3-YL]METHANONES

CROSS REFERENCE TO RELATED APPLICATION

This application is a continuation-in-part of our co-pending application, Ser. No. 506,966, filed June 23, 1983, now abandoned.

SUMMARY OF THE INVENTION

This invention relates to new organic compounds which are aryl or heteroaryl[7-(aryl or heteroaryl)-pyrazolo[1,5-a]pyrimidin-3-yl]methanones which are useful as anxiolytic or antiepileptic agents as well as sedative-hypnotic and skeletal muscle relaxant agents. This invention also relates to these methods of using the novel compounds, to compositions of matter containing them as the active ingredient and to processes for their production.

DETAILED DESCRIPTION OF THE INVENTION

In accordance with this invention, the novel compounds are represented by the following structural formula:

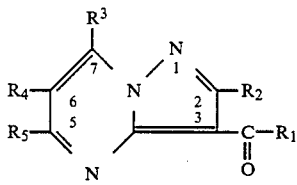

wherein $R_1$ is selected from the group consisting of unsubstituted phenyl; phenyl mono- or di-substituted by halogen, alkoxy($C_1$–$C_3$) or alkyl($C_1$–$C_3$); phenyl mono-substituted by trifluoromethyl, alkylthio($C_1$–$C_3$), alkylamino($C_1$–$C_3$), dialkylamino($C_1$–$C_3$), methylenedioxy, alkylsulfonyl($C_1$–$C_3$) or alkanoylamino($C_1$–$C_3$); naphthalenyl; thiazolyl; biphenyl; thienyl; furanyl; pyridinyl; substituted thiazolyl; substituted biphenyl; substituted thienyl; and substituted pyridinyl wherein the substituents are selected from one or two of the group consisting of halogen, alkoxy($C_1$–$C_3$) and alkyl(-$C_1$–$C_3$); $R_2$, $R_4$ and $R_5$ are each selected from the group consisting of hydrogen and alkyl($C_1$–$C_3$); and $R_3$ is selected from the group consisting of unsubstituted phenyl, phenyl mono-substituted by halogen, trifluoromethyl, alkoxy($C_1$–$C_3$), amino, alkyl($C_1$–$C_3$), alkylamino($C_1$–$C_6$), dialkylamino($C_1$–$C_3$), alkanoylamino($C_1$–$C_6$), N-alkyl($C_1$–$C_6$)alkanoylamino($C_1$–$C_6$), cyano or alkylthio($C_1$–$C_3$); furanyl; thienyl; pyridinyl; and pyridine-1-oxide.

The most preferred compounds of this invention of particular interest are those compounds of the above formula wherein $R_3$ is 3-(trifluoromethyl)phenyl, 3-pyridinyl or 4-pyridinyl especially when $R_1$ is 2-furanyl and $R_2$, $R_4$ and $R_5$ are each hydrogen. Also, the compounds of major interest are selected from the above formula wherein $R_3$ is 3-(trifluoromethyl)phenyl, 3-pyridinyl, 4-pyridinyl, 3-[N-alkyl($C_1$–$C_6$)alkanoylamino($C_1$–$C_6$)]phenyl or 3-[alkylamino($C_1$–$C_6$)], when $R_1$ is unsubstituted phenyl; phenyl substituted by 4-methyl, 4-ethyl, 4-methoxy, 3,4-dimethoxy or 4-dimethylamino; 2-furanyl; 2-thienyl; 2-pyridinyl; or 4-pyridinyl; and $R_2$, $R_4$ and $R_5$ are each hydrogen.

Other representative compounds of the invention herein are as follows:

2-furanyl[7-(2-furanyl)pyrazolo[1,5-a]pyrimidin-3-yl]methanone
2-furanyl[7-(2-thienyl)pyrazolo[1,5-a]pyrimidin-3-yl]methanone
[7-(2-furanyl)pyrazolo[1,5-a]pyrimidin-3-yl]-2-pyridinyl-methanone
[7-(2-furanyl)pyrazolo[1,5-a]pyrimidin-3-yl]-3-pyridinyl-methanone
[7-(2-furanyl)pyrazolo[1,5-a]pyrimidin-3-yl]-4-pyridinyl-methanone
[4-(dimethylamino)phenyl][7-(2-furanyl)pyrazolo[1,5-a]pyrimidin-3-yl]methanone
2-thienyl[7-(2-thienyl)pyrazolo[1,5-a]pyrimidin-3-yl]methanone
3-pyridinyl[7-(2-thienyl)pyrazolo[1,5-a]pyrimidin-3-yl]methanone
[4-(dimethylamino)phenyl][7-(2-thienyl)pyrazolo[1,5-a]pyrimidin-3-yl]methanone
2-furanyl[7-(3-thienyl)pyrazolo[1,5-a]pyrimidin-3-yl]methanone
2-thienyl[7-(3-thienyl)pyrazolo[1,5-a]pyrimidin-3-yl]methanone
3-pyridinyl[7-(3-thienyl)pyrazolo[1,5-a]pyrimidin-3-yl]methanone
4-pyridinyl[7-(3-thienyl)pyrazolo[1,5-a]pyrimidin-3-yl]methanone
[4-(dimethylamino)phenyl][7-(3-thienyl)pyrazolo[1,5-a]pyrimidin-3-yl]methanone
(3,4-dimethylphenyl)[7-(4-pyridinyl)pyrazolo[1,5-a]pyrimidin-3-yl]methanone
(3,4-dimethylphenyl)[7-(3-pyridinyl)pyrazolo[1,5-a]pyrimidin-3-yl]methanone
(3,4-dimethylphenyl)[7-[3-(trifluoromethyl)phenyl]-pyrazolo[1,5-a]pyrimidin-3-yl]methanone
(4-dimethylaminophenyl)[7-(4-pyridinyl)pyrazolo[1,5-a]pyrimidin-3-yl]methanone
(4-dimethylaminophenyl)[7-(3-pyridinyl)pyrazolo[1,5-a]pyrimidin-3-yl]methanone
(4-dimethylaminophenyl)[7-[3-(trifluoromethyl)-phenyl]pyrazolo[1,5-a]pyrimidin-3-yl]methanone
2-thiazolyl[7-[3-trifluoromethyl)phenyl]pyrazolo[1,5-a]pyrimidin-3-yl]methanone
(5-methyl-2-thienyl)[7-[3-(trifluoromethyl)phenyl]-pyrazolo[1,5-a]pyrimidin-3-yl]methanone
(5-methyl-2-thienyl)[7-(3-pyridinyl)pyrazolo[1,5-a]pyrimidin-3-yl]methanone
(5-methyl-2-thienyl)[7-(4-pyridinyl)pyrazolo[1,5-a]pyrimidin-3-yl]methanone
(5-chloro-2-thienyl)[7-[3-(trifluoromethyl)phenyl]-pyrazolo[1,5-a]pyrimidin-3-yl]methanone
(5-chloro-2-thienyl)[7-(3-pyridinyl)pyrazolo[1,5-a]pyrimidin-3-yl]methanone
(5-chloro-2-thienyl)[7-(4-pyridinyl)pyrazolo[1,5-a]pyrimidin-3-yl]methanone
(5-bromo-2-thienyl)[7-[3-(trifluoromethyl)phenyl]-pyrazolo[1,5-a]pyrimidin-3-yl]methanone
(5-bromo-2-thienyl)[7-(3-pyridinyl)pyrazolo[1,5-a]pyrimidin-3-yl]methanone
(5-bromo-2-thienyl)[7-(4-pyridinyl)pyrazolo[1,5-a]pyrimidin-3-yl]methanone
(3-chloro-2-pyridinyl)[7-[3-(trifluoromethyl)phenyl]-pyrazolo[1,5-a]pyrimidin-3-yl]methanone
(3-chloro-2-pyridinyl)[7-(3-pyridinyl)pyrazolo[1,5-a]pyrimidin-3-yl]methanone (3-chloro-2-pyridinyl)[7-(4-pyridinyl)pyrazolo[1,5-a]pyrimidin-3-yl]methanone
(3-fluoro-2-pyridinyl)[7-[3-(trifluoromethyl)phenyl]pyrazolo[1,5-a]pyrimidin-3-yl]methanone
(3-fluoro-2-pyridinyl)[7-(3-pyridinyl)pyrazolo[1,5-a]pyrimidin-3-yl]methanone
(3-fluoro-2-pyridinyl)[7-(4-pyridinyl)pyrazolo[1,5-a]pyrimidin-3-yl]methanone
(5-chloro-2-pyridinyl)[7-[3-(trifluoromethyl)phenyl]pyrazolo[1,5-a]pyrimidin-3-yl]methanone
(5-chloro-2-pyridinyl)[7-(3-pyridinyl)pyrazolo[1,5-a]pyrimidin-3-yl]methanone
(5-chloro-2-pyridinyl)[7-(4-pyridinyl)pyrazolo[1,5-a]pyrimidin-3-yl]methanone
(5-fluoro-2-pyridinyl)[7-(3-pyridinyl)pyrazolo[1,5-a]pyrimidin-3-yl]methanone
(5-fluoro-2-pyridinyl)[7-[3-(trifluoromethyl)phenyl]pyrazolo[1,5-a]pyrimidin-3-yl]methanone
(3-methyl-2-pyridinyl)[7-[3-(trifluoromethyl)phenyl]pyrazolo[1,5-a]pyrimidin-3-yl]methanone
(3-methyl-2-pyridinyl)[7-(3-pyridinyl)pyrazolo[1,5-a]pyrimidin-3-yl]methanone
(3-methyl-2-pyridinyl)[7-(4-pyridinyl)pyrazolo[1,5-a]pyrimidin-3-yl]methanone
(5-methyl-2-pyridinyl)[7-[3-(trifluoromethyl)phenyl]pyrazolo[1,5-a]pyrimidin-3-yl]methanone
(2-fluorophenyl)[7-[3-(trifluoromethyl)phenyl]pyrazolo[1,5-a]pyrimidin-3-yl]methanone
(2-fluorophenyl)[7-(3-pyridinyl)pyrazolo[1,5-a]pyrimidin-3-yl]methanone
(2-fluorophenyl)[7-(4-pyridinyl)pyrazolo[1,5-a]pyrimidin-3-yl]methanone
(3-pyridinyl)[7-[3-(trifluoromethyl)phenyl]pyrazolo[1,5-a]pyrimidin-3-yl]methanone
(3-pyridinyl)[7-(3-pyridinyl)pyrazolo[1,5-a]pyrimidin-3-yl]methanone
(3-pyridinyl)[7-(4-pyridinyl)pyrazolo[1,5-a]pyrimidin-3-yl]methanone
(5-methyl-3-pyridinyl)[7-[3-(trifluoromethyl)phenyl]pyrazolo[1,5-a]pyrimidin-3-yl]methanone
(5-methyl-3-pyridinyl)[7-(3-pyridinyl)pyrazolo[1,5-a]pyrimidin-3-yl]methanone
(5-methyl-3-pyridinyl)[7-(4-pyridinyl)pyrazolo-[1,5-a]pyrimidin-3-yl]methanone
(6-methyl-3-pyridinyl)[7-[3-(trifluoromethyl)phenyl]pyrazolo[1,5-a]pyrimidin-3-yl]methanone
(6-methyl-3-pyridinyl)[7-(3-pyridinyl)pyrazolo[1,5-a]pyrimidin-3-yl]methanone
(6-methyl-3-pyridinyl)[7-(4-pyridinyl)pyrazolo[1,5-a]pyrimidin-3-yl]methanone
(3-thienyl)[7-[3-(trifluoromethyl)phenyl]pyrazolo[1,5-a]pyrimidin-3-yl]methanone
[7-(3-pyridinyl)pyrazolo[1,5-a]pyrimidin-3-yl]-3-thienyl-methanone
(3-furanyl)[7-[3-(trifluoromethyl)phenyl]pyrazolo[1,5-a]pyrimidin-3-yl]methanone
(3-furanyl)[7-(4-pyridinyl)pyrazolo[1,5-a]pyrimidin-3-yl]methanone
(3-methoxy-2-pyridinyl)[7-[3-(trifluoromethyl)phenyl]pyrazolo[1,5-a]pyrimidin-3-yl]methanone
(3-methoxy-2-pyridinyl)[7-(3-pyridinyl)pyrazolo[1,5-a]pyrimidin-3-yl]methanone
(4-methoxy-2-pyridinyl)[7-[3-(trifluoromethyl)phenyl]pyrazolo[1,5-a]pyrimidin-3-yl]methanone
(4-methoxy-2-pyridinyl)[7-(3-pyridinyl)pyrazolo[1,5-a]pyrimidin-3-yl]methanone
(4-methoxy-2-pyridinyl)[7-(4-pyridinyl)pyrazolo[1,5-a]pyrimidin-3-yl]methanone
(4-methyl-2-pyridinyl)[7-(3-pyridinyl)pyrazolo[1,5-a]pyrimidin-3-yl]methanone
(4-fluoro-2-pyridinyl)[7-(3-pyridinyl)pyrazolo[1,5-a]pyrimidin-3-yl]methanone
(5-methoxy-2-pyridinyl)[7-(3-pyridinyl)pyrazolo[1,5-a]pyrimidin-3-yl]methanone
(5-fluoro-3-pyridinyl)[7-(3-pyridinyl)pyrazolo[1,5-a]pyrimidin-3-yl]methanone
(5-ethoxy-3-pyridinyl)[7-(3-pyridinyl)pyrazolo[1,5-a]pyrimidin-3-yl]methanone
(5-ethoxy-2-pyridinyl)[7-(3-pyridinyl)pyrazolo[1,5-a]pyrimidin-3-yl]methanone
(5-methoxy-3-pyridinyl)[7-(3-pyridinyl)pyrazolo[1,5-a]pyrimidin-3-yl]methanone
(6-methoxy-3-pyridinyl)[7-(3-pyridinyl)pyrazolo[1,5-a]pyrimidin-3-yl]methanone
(6-methoxy-3-pyridinyl)[7-[3-(trifluoromethyl)phenyl]pyrazolo[1,5-a]pyrimidin-3-yl]methanone
4-pyridinyl[7-(3-pyridinyl)pyrazolo[1,5-a]pyrimidin-3-yl]methanone
4-pyridinyl[7-[3-(trifluoromethyl)phenyl]pyrazolo[1,5-a]pyrimidin-3-yl]methanone The instant invention is additionally concerned with the methods of treating anxiety or epilepsy and inducing a sedative-hypnotic or skeletal muscle relaxation effect in mammals employing the above-described compounds, to compositions of matter containing these compounds and processes for their production.

The novel compounds of this invention may be readily prepared as set forth in the following reaction scheme:

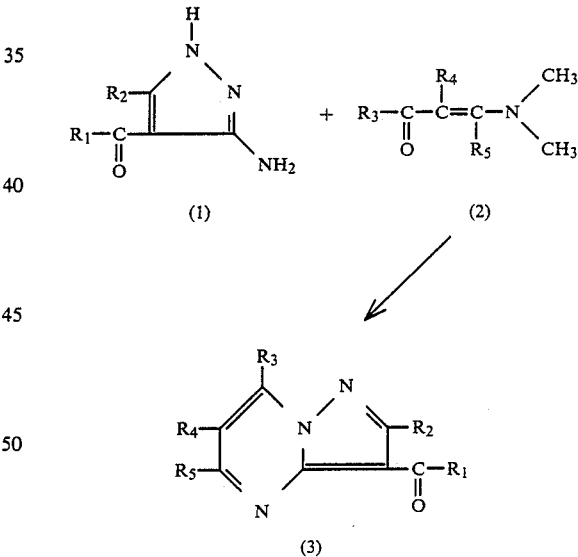

wherein $R_1$, $R_2$, $R_3$, $R_4$, and $R_5$ are as described above. The reaction of an appropriately substituted pyrazole (1) and an appropriately substituted 3-dimethylamino-1-(aryl) or (heteroaryl)-2-propen-1-one (2) in glacial acetic acid at reflux temperature for several hours, followed by solvent removal, partitioning of the residue between saturated aqueous sodium bicarbonate and methylene chloride, passage of the organic layer through hydrous magnesium silicate and the addition of hexane to the refluxing eluate produces the desired products (3).

Products where $R_3$ is a pyridine-1-oxide may be prepared by treating the compounds (3) where $R_3$ is pyridine with m-chloroperbenzoic acid in methylene chloride with stirring for several hours, collecting the solid, slurrying it in saturated aqueous sodium bicarbonate and boiling in water.

The substituted 3-dimethylamino-1-(aryl) or (heteroaryl)-2-propen-1-ones (2) are disclosed in one or more of U.S. Pat. Nos. 4,178,449; 4,281,000; and 4,236,005.

The substituted pyrazoles (1) are the subject of copending application, Ser. No. 507,317, filed June 23, 1983.

Pyrazolo[1,5-a]pyrimidines are prepared by condensation of 3-aminopyrazoles and substituted 3-aminopyrazoles with 1,3-dicarbonyl compounds as described in J. Med. Chem., 18, 645 (1974); J. Med. Chem., 18, 460 (1975); J. Med. Chem., 20, 386 (1977); Synthesis, 673 (1982) and references contained therein.

The 7-aryl and 7-heteroaryl[1,5-a]pyrimidines of this invention, which contain a 3-aroyl group, are synthesized by condensation of 1-aryl or 1-heteroaryl-1,3-dicarbonyl compounds with 3-amino-4-aroylpyrazoles.

The 3-aryl-1,3-dicarbonyl compounds useful in condensations with the appropriate 3-amino-4-aroylpyrazoles are represented by the following structural formulae (4 to 8):

where G is —O— or —N—D, where D is alkyl($C_1$-$C_6$), benzyl, benzoyl or alkanoyl($C_2$-$C_7$).

The structure represented by formula (4) is a 1-aryl-1,3-dicarbonyl derivative which may enolize to give two enol structures represented by formula (4a) and (4b). The extent of enolization is dependent on the substituent $R_5$. When $R_5$ is hydrogen, the structure (4) represents an α-formyl ketone derivative which exists principally as the enolized form (4a). Such hydroxymethyleneketones (4a) are prepared by formylation of arylketones (6) with alkali metal alkoxides and alkyl formates such as methyl formate, ethyl formate and the like. The preparation of hydroxymethyleneketones is illustrated in Scheme 1.

The intermediate alkali metal salts of hydroxymethyleneketones (10) can be acylated by reaction with acid chlorides or anhydrides such as alkanoyl chlorides, benzoyl chloride, alkanoic acid anhydrides or benzoic anhydride to give O-acyl derivatives (12). Neutralization of the alkali metal salts (10) with acids such as acetic acid, hydrochloric acid and the like affords hydroxymethyleneketones (11). Either the alkali metal salts (10), the hydroxymethyleneketones (11), or the O-acylated derivatives (12) or hydroxymethyleneketones may be condensed with 3-amino-4-aroylpyrazoles

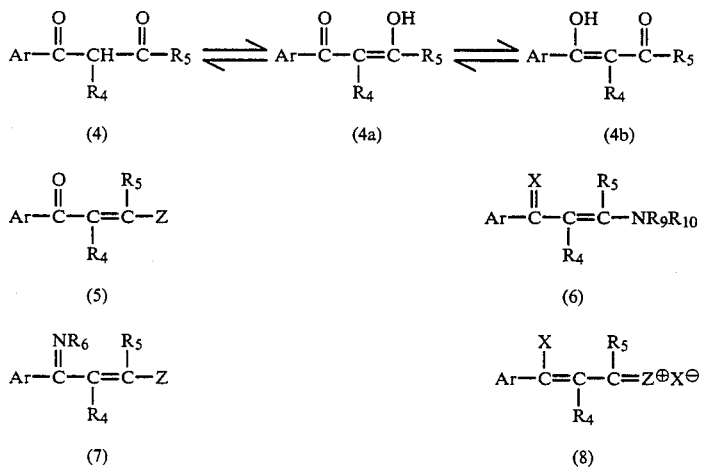

wherein $R_4$ and $R_5$ are hydrogen or alkyl($C_1$-$C_3$); $R_6$ is alkyl($C_1$-$C_6$), cyclohexyl, cyclopentyl, phenyl, or —$(CH_2)_m$-phenyl where m is an integer 1-3; X is chloro, bromo, $OR_7$ or $SR_7$, where $R_7$ is alkyl($C_1$-$C_6$); Z is $SR_7$, $OR_8$, $NR_9R_{10}$ or $NHR_6$ wherein $R_8$ is hydrogen, alkyl($C_1$-$C_{10}$), —$(CH_2)_n$-phenyl where n is an integer 1-3, alkanoyl($C_2$-$C_{10}$), benzoyl or carboalkoxy($C_2$-$C_{10}$); and $R_9$ and $R_{10}$ are individually selected from hydrogen, alkyl($C_1$-$C_{10}$), phenyl and when taken together with the nitrogen atom to which they are attached form

where p is an integer 4-6, or

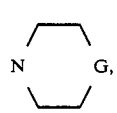

(1), under acidic or neutral conditions, in inert solvents, to give the novel 3-aroyl-7-aryl(or heteroaryl)-pyrazolo[1,5-a]pyrimidines (13) of this invention wherein $R_4$ is hydrogen or alkyl($C_1$-$C_3$) and $R_5$ is hydrogen.

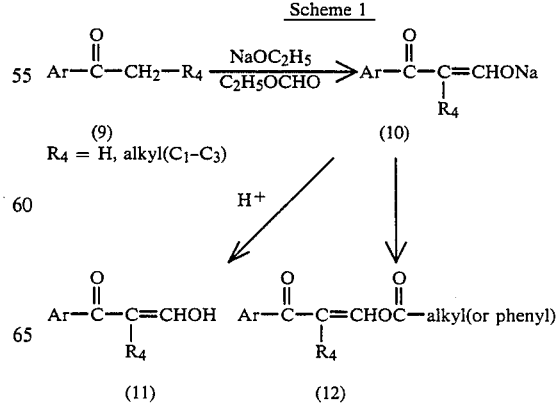

Scheme 1 -continued

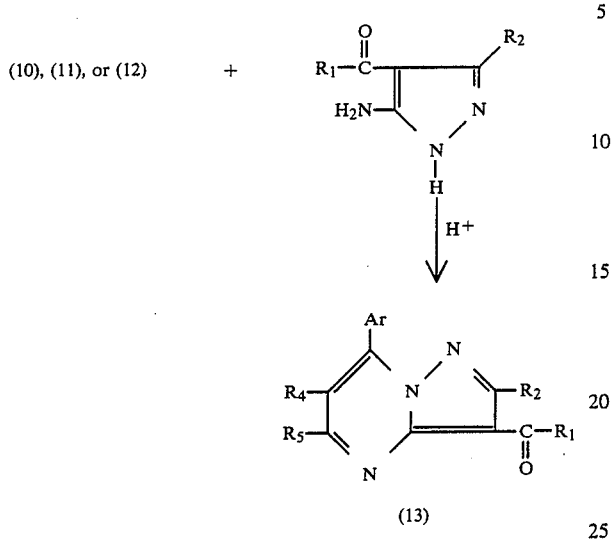

$R_4$ = hydrogen or alkyl($C_1$–$C_3$)
$R_5$ = hydrogen

The hydroxymethyleneketones (11) may be converted by the procedure of Scheme 2 to other aldehyde equivalents such as alkoxymethyleneketones (14), alkylthiomethyleneketones (15), or aminomethyleneketones (16). These aldehyde equivalents of hydroxymethyleneketones on condensation with 3-amino-4-aroylpyrazoles give 3-aroyl-7-aryl(or heteroaryl)-pyrazolo[1,5-a]pyrimidines (13), wherein $R_4$ is hydrogen or alkyl($C_1$–$C_3$) and $R_5$ is hydrogen.

Scheme 2

$$Ar-\overset{O}{\underset{}{C}}-\underset{R_4}{C}=CHOH \xrightarrow{alkyl-OH} Ar-\overset{O}{\underset{}{C}}-\underset{R_4}{C}=CH-O-alkyl$$

(11) → (14)

HNR_9R_{10} or NH_2R_5

$$\xrightarrow{alkyl-SH} Ar-\overset{O}{\underset{}{C}}-\underset{R_4}{C}=CH-S-alkyl$$

(15)

$$Ar-\overset{O}{\underset{}{C}}-\underset{R_4}{C}=CHNR_9R_{10}(\text{or } NHR_6)$$

(16)

Scheme 2 -continued (14), (15), or (16) + structure with $R_1-C(=O)$, $H_2N$, $R_2$, N, N–H (1)

↓ structure (13) with Ar, $R_4$, $R_5$, N, N, N, $R_2$, C(=O)–$R_1$ (13)

$R_4$ = hydrogen or alkyl($C_1$–$C_3$)
$R_5$ = hydrogen

Thus, hydroxymethyleneketones and derivatives which are chemical equivalents of hydroxymethyleneketones react under acidic or neutral conditions with 3-amino-4-aroylpyrazoles to give novel 3-aroyl-7-aryl(or heteroaryl)pyrazolo[1,5-a]pyrimidines.

Other intermediates which are chemical equivalents of hydroxymethyleneketones (11) are 3-(dialkylamino)-1-aryl or (heteroaryl)-2-propen-1-ones (17). Such N,N-(dialkylamino)methyleneketones (enaminones) (17) are prepared by reaction of arylketones (9) with N,N-dimethylformamide-dialkoxyacetals or N,N-dimethylacetamide-dialkoxyacetals. Other acetals of N,N-dialkylformamides or acetals of N,N-dialkylacetamides, such as N,N-diethylformamide-dimethoxyacetal, N,N-dibutylformamide-diethoxyacetal, N,N-diethylacetamide-diethoxyacetal and the like may also be used in reactions with arylketones (9) to give aminomethylene ketone derivatives (17), (20) and (21). These derivatives are chemical equivalents of hydroxymethyleneketones(α-formylketones) and they react with 3-amino-4-aroylpyrazoles (1) to give 3-aroyl-7-aryl(or heteroaryl)-pyrazolo[1,5-a]pyrimidines as shown in Scheme 3.

The reactions in Scheme 3 illustrate the methods for synthesizing derivatives with an alkyl group at the C-5 position [$R_5$, formula (23)] or at the C-6 position [$R_4$, formula (18)] of the pyrazolo[1,5-a]pyrimidine nucleus. This method also allows the preparation of derivatives (22) wherein $R_4$ and $R_5$ in formula (13) are both hydrogen. The reaction of ketones (9) and (19) with acetals of N,N-dialkylformamides or acetals of N,N-dialkylacetamides can be carried out in inert solvents or without a solvent.

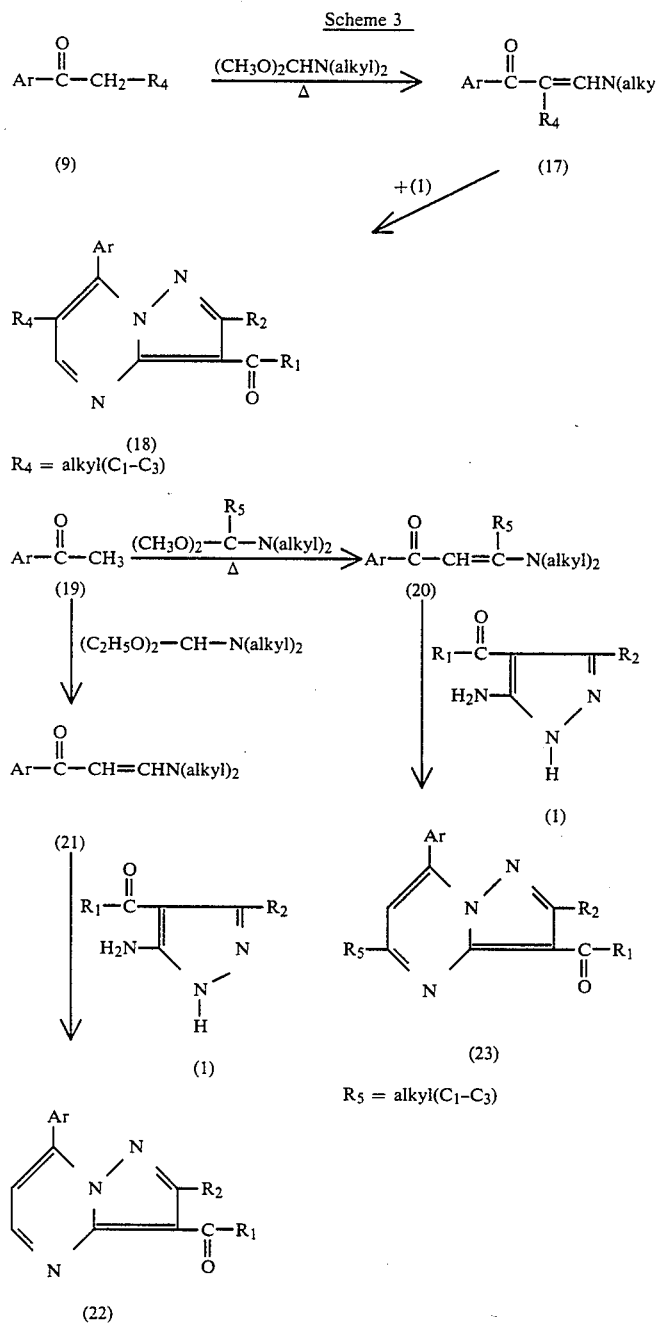

Scheme 3

3-Aryl-3-chloroacroleins (24) may also be used as intermediates for the condensation of 3-amino-4-aroyl(or heteroaroyl)pyrazoles to give pyrazolo[1,5-a]pyrimidines as described in Scheme 4. The intermediates (24) are synthesized by the reaction of aryl ketones (9) with N,N-dimethylformamide-phosphorus oxychloride (Vilsmeier reagent) as described by J. A. Virgilio and E. Heilweil, Org. Prep., Proced. Int. 14 (1-2), pp 9-20 (1982) and references cited therein, and M. Weissenfels, et al., Z. Chem., 6, 471 (1966).

The reaction involves a formylation of the ketone followed by chlorination of the initially formylated product. Alternatively, reaction of N,N-dialkylaminomethyleneketones (enaminones) (17) with N,N-dimethylformamide-phosphorus oxychloride affords intermediates (25) which give, on hydrolysis, 3-aryl-3-chloroacroleins (24). Substitution of phosphorus oxybromide for phosphorus oxychloride in the reactions of Scheme 4 affords the corresponding 3-aryl-3-bromoacroleins which may also be condensed with 3-amino-4-aroyl(or heteroaroyl)pyrazoles to give pyrazolo[1,5-a]pyrimidines. The intermediates (25) may be reacted with 3-amino-4-aroyl(or heteroaroyl)pyrazoles to afford pyrazolo[1,5-a]pyrimidines (18).

Scheme 4

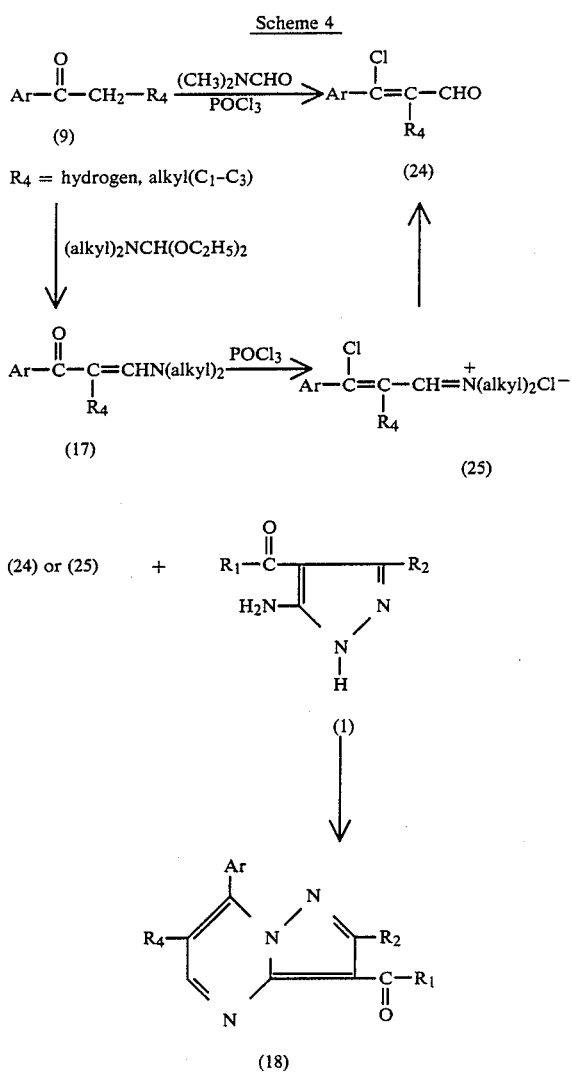

1-Aryl-1,3-diketones illustrated by structural formula (26) as shown in Scheme 5, react with dialkylamines such as pyrrolidine, dimethylamine, diethylamine and the like to form enaminones (27). Reaction of compounds of structure type (27) with 3-amino-4-aroylpyrazoles (1) under acidic reaction conditions gives pyrazolo[1,5-a]pyrimidines (28).

Scheme 5

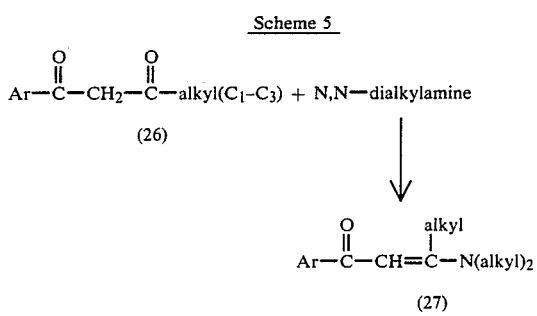

Scheme 5 -continued

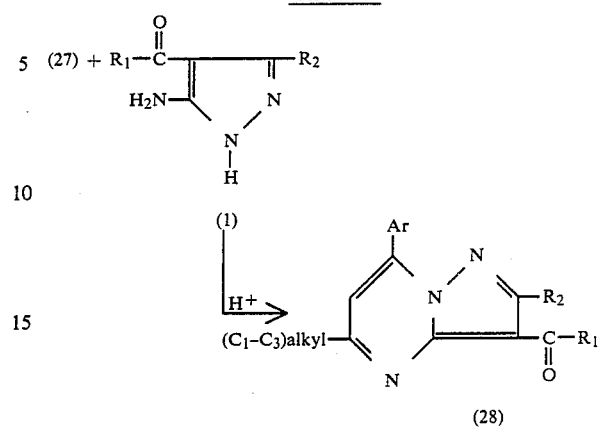

1-Aroyl-1-propynones (29) react with 3-amino-4-aroylpyrazoles (1) in alkanols such as methanol, ethanol, propanol, butanol and the like under catalysis with acids such as p-toluenesulfonic acid, acetic acid, boron trifluoride and the like at 50° to 100° C. to give 7-arylpyrazolo[1,5-a]pyrimidines (30) as shown in scheme 6. Other suitable solvents for the reaction are benzene, toluene, xylene, dimethylformamide, dimethylacetamide, tetrahydrofuran, dioxane and the like.

Scheme 6

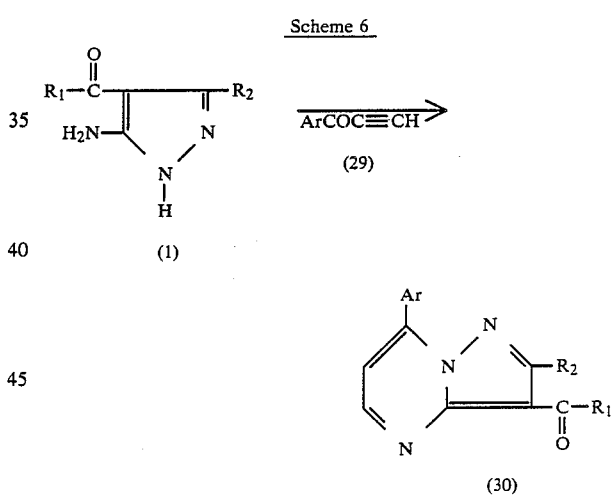

The preferred reaction conditions for condensation of hydroxymethylene ketones (11), 3-(dialkylamino)-1-aryl(or heteroaryl)-2-propen-1-one (17) and the like with 3-amino-4-aroylpyrazoles (1) are heating at 80°–130° C. in glacial acetic acid for 1–10 hours. Alternatively, the condensation reactions may be carried out with inert cosolvents in the presence of glacial acetic acid. Suitable solvents are dioxane, tetrahydrofuran, toluene, xylene, chloroform, carbon tetrachloride and the like. The novel pyrazolo[1,5-a]pyrimidines of this invention may also be prepared by reaction of 3-amino-4-aroylpyrazoles with an appropriate 3-alkoxy, 3-hydroxy, 3-acetoxy, 3-alkylthio, or 3-benzyloxy-1-(aryl or heteroaryl)-2-propen-1-one in inert organic solvents such as lower alkanols, dioxane, tetrahydrofuran, toluene and the like at the reflux temperature thereof and with or without 1 to 10 equivalents of an acid as catalyst. Suitable acid catalysts are glacial acetic acid, hydrochloric acid, trifluoroacetic acid and the like.

The novel compounds of the present invention possess central nervous system activity at nontoxic doses and as such are useful as anxiolytic agents. That is, they produce certain responses in standard tests with laboratory animals which are known to correlate well with relief of anxiety in man. Furthermore, these compounds have been shown by biological data to be useful as antiepileptic agents, particularly in the treatment of grand mal seizures as well as sedative-hypnotic and skeletal muscle relaxant agents.

The anti-anxiety and anticonvulsant properties of the novel compounds of the present invention have been established in a test which indicates anxiolytic and antiepileptic activity by the measure of protection from convulsions resulting from the administration of pentylenetetrazole. Single or graded dose levels of the test compounds were administered orally or intraperitoneally in a 2% starch vehicle, containing 0.5% v/v polyethylene glycol and one drop of Polysorbate 80 to groups of at least 4 rats. At 30 or 60 minutes, the rats were treated intravenously with pentylenetetrazole at a dose of 23 mg/kg of body weight. This dose is estimated to cause clonic seizures in 99% of unprotected rats. It has been reported [R. T. Hill and D. H. Tedeschi, "Animal Testing and Screening Procedures in Evaluating Psychotropic Drugs" in "An Introduction to Psychopharmacology", Eds. R. R. Rech and K. E. Moore, Raven Press, New York, pp 237-288 (1971)] that there is a high degree of correlation between antagonism of pentylenetetrazole seizures in rats and anti-anxiety or anticonvulsant effects in higher warm-blooded animals. The results of this test on representative compounds of the present invention are shown in Table I.

TABLE I

Protection Against Clonic Seizures Caused by Pentylenetetrazole in Rats

| Compound | Dose (mg/kg) | % of Rats Protected |
|---|---|---|
| phenyl[7-(3-pyridinyl)pyrazolo[1,5-a]pyrimidin-3-yl]methanone | 25.0 | 100 |
| (4-fluorophenyl)[7-(4-pyridinyl)pyrazolo[1,5-a]pyrimidin-3-yl]methanone | 25.0 | 100 |
| phenyl[7-(4-pyridinyl)pyrazolo[1,5-a]pyrimidin-3-yl]methanone | 25.0 | 100 |
| phenyl[7-[3-(trifluoromethyl)phenyl]pyrazolo[1,5-a]pyrimidin-3-yl]methanone | 25.0 | 100 |
| (4-fluorophenyl)[7-[3-(trifluoromethyl)phenyl]pyrazolo[1,5-a]pyrimidin-3-yl]methanone | 12.5 | 38 |
| (4-fluorophenyl)[7-(3-pyridinyl)pyrazolo[1,5-a]pyrimidin-3-yl]methanone | 25.0 | 63 |
| [7-(3,4-dimethoxyphenyl)-5-methylpyrazolo[1,5-a]pyrimidin-3-yl](4-fluorophenyl)methanone | 25.0 | 25 |
| 2-thienyl[7-[3-(trifluoromethyl)phenyl]pyrazolo[1,5-a]pyrimidin-3-yl]methanone | 25.0 | 100 |
| 2-furanyl[7-(4-pyridinyl)pyrazolo[1,5-a]pyrimidin-3-yl]methanone | 25.0 | 25 |
| [7-(3-pyridinyl)pyrazolo[1,5-a]pyrimidin-3-yl]-2-thienyl-methanone | 25.0 | 75 |
| 2-furanyl[7-[3-(trifluoromethyl)phenyl]pyrazolo[1,5-a]pyrimidin-3-yl]methanone | 25.0 | 100 |
| 2-furanyl[7-(3-pyridinyl)pyrazolo[1,5-a]pyrimidin-3-yl]methanone | 25.0 | 100 |
| [2-methyl-7-(3-pyridinyl)pyrazolo[1,5-a]pyrimidin-3-yl]phenyl-methanone | 25.0 | 50 |
| [7-(3,4-dichlorophenyl)-5-methylpyrazolo[1,5-a]pyrimidin-3-yl]phenyl-methanone | 25.0 | 25 |
| (4-methylphenyl)[7-(3-pyridinyl)pyrazolo[1,5-a]pyrimidin-3-yl]methanone | 25.0 | 100 |
| (4-methylphenyl)[7-(4-pyridinyl)pyrazolo[1,5-a]pyrimidin-3-yl]methanone | 25.0 | 50 |
| (4-methylphenyl)[7-[3-(trifluoromethyl)phenyl]pyrazolo[1,5-a]pyrimidin-3-yl]methanone | 25.0 | 50 |
| phenyl[7-(4-pyridinyl)pyrazolo[1,5-a]pyrimidin-3-yl]methanone, pyridine-1-oxide | 25.0 | 100 |
| 2-pyridinyl[7-(3-pyridinyl)pyrazolo[1,5-a]pyrimidin-3-yl]methanone | 25.0 | 75 |
| 2-pyridinyl[7-[3-(trifluoromethyl)phenyl]pyrazolo[1,5-a]pyrimidin-3-yl]methanone | 25.0 | 100 |
| 2-pyridinyl[7-(4-pyridinyl)pyrazolo[1,5-a]pyrimidin-3-yl]methanone | 25.0 | 100 |
| (3-fluorophenyl)[7-(4-pyridinyl)pyrazolo[1,5-a]pyrimidin-3-yl]methanone | 25.0 | 100 |
| [7-(4-fluorophenyl)pyrazolo[1,5-a]pyrimidin-3-yl]phenyl-methanone | 25.0 | 100 |
| [7-(3,5-dichlorophenyl)pyrazolo[1,5-a]pyrimidin-3-yl]phenyl-methanone | 25.0 | 25 |
| (3-fluorophenyl)[7-(3-pyridinyl)pyrazolo)[1,5-a]pyrimidin-3-yl]methanone | 25.0 | 100 |
| (4-fluorophenyl)[7-(2-pyridinyl)pyrazolo[1,5-a]pyrimidin-3-yl]methanone | 25.0 | 50 |
| (2-chlorophenyl)[7-(3-pyridinyl)pyrazolo[1,5-a]pyrimidin-3-yl]methanone | 25.0 | 100 |
| (4-fluorophenyl)[7-(2-fluorophenyl)pyrazolo[1,5-a]pyrimidin-3-yl]methanone | 25.0 | 50 |
| (4-fluorophenyl)[5-methyl-7-[3-(trifluoromethyl)phenyl]pyrazolo[1,5-a]pyrimidin-3-yl]methanone | 25.0 | 25 |
| (4-fluorophenyl)[7-[4-(trifluoromethyl)phenyl]pyrazolo[1,5-a]pyrimidin-3-yl]methanone | 25.0 | 50 |
| 4-[3-(4-fluorobenzoyl)pyrazolo[1,5-a]pyrimidin-7-yl]benzonitrile | 25.0 | 50 |
| [7-(4-pyridinyl)pyrazolo[1,5-a]pyrimidin-3-yl](3,4,5-trimethoxyphenyl)-methanone | 25.0 | 25 |
| [6-methyl-7-(4-pyridinyl)pyrazolo[1,5-a]pyrimidin-3-yl]phenyl-methanone | 25.0 | 100 |
| (6-methyl-7-phenylpyrazolo[1,5-a]pyrimidin-3-yl)phenyl-methanone | 25.0 | 25 |
| 3-furanyl[7-(3-pyridinyl)pyrazolo[1,5-a]pyrimidin-3-yl]methanone | 25.0 | 100 |
| [7-(3-pyridinyl)pyrazolo[1,5-a]pyrimidin-3-yl](3,4,5-trimethoxyphenyl)-methanone | 25.0 | 25 |
| (3,4-dimethoxyphenyl)[7-(3-pyridinyl)pyrazolo[1,5-a]pyrimidin-3-yl]methanone | 25.0 | 87 |
| (3,4-dimethoxyphenyl)[7-[3-(trifluoromethyl)phenyl]pyrazolo[1,5-a]pyrimidin-3-yl]methanone | 25.0 | 50 |
| (3,4-dimethoxyphenyl)[7-(3,4,5-trimethoxyphenyl)pyrazolo[1,5-a]pyrimidin-3-yl]methanone | 25.0 | 75 |
| (3-methylphenyl)[7-(3-pyridinyl)pyrazolo[1,5-a]pyrimidin-3-yl]methanone | 25.0 | 100 |
| (3,4-dimethoxyphenyl)[7-(4-pyridinyl)pyrazolo[1,5-a]pyrimidin-3-yl]methanone | 25.0 | 50 |
| (3-methylphenyl)[7-(4-pyridinyl)pyrazolo[1,5-a]pyrimidin-3-yl]methanone | 25.0 | 100 |
| (3-methylphenyl)[7-[3-(trifluoromethyl)phenyl]pyrazolo[1,5-a]pyrimidin-3-yl]methanone | 25.0 | 25 |
| (3-methylphenyl)[7-(3-methylphenyl)pyrazolo[1,5-a]pyrimidin-3-yl]methanone | 25.0 | 25 |
| (4-chlorophenyl)[5-methyl-7-[3-(trifluoromethyl)phenyl]pyrazolo[1,5-a]pyrimidin-3-yl]methanone | 25.0 | 25 |
| [5-methyl-7-(4-pyridinyl)pyrazolo[1,5-a]pyrimidin-3-yl]phenyl-methanone, pyridine-1-oxide | 25.0 | 25 |
| [7-(4-fluorophenyl)pyrazolo[1,5-a]pyrimidin-3-yl]-2-pyridinyl-methanone | 25.0 | 50 |
| (4-fluorophenyl)[7-(4-fluorophenyl)pyrazolo[1,5-a]pyrimidin-3-yl]methanone | 25.0 | 75 |

TABLE I-continued

Protection Against Clonic Seizures Caused by Pentylenetetrazole in Rats

| Compound | Dose (mg/kg) | % of Rats Protected |
|---|---|---|
| (4-methoxyphenyl)[7-(3-pyridinyl)pyrazolo[1,5-a]pyrimidin-3-yl]methanone | 25.0 | 100 |
| [7-(4-fluorophenyl)pyrazolo[1,5-a]pyrimidin-3-yl][3-(trifluoromethyl)phenyl]methanone | 25.0 | 25 |
| (4-methoxyphenyl)[7-(4-pyridinyl)pyrazolo[1,5-a]pyrimidin-3-yl]methanone | 25.0 | 25 |
| (3-methoxyphenyl)[7-(4-pyridinyl)pyrazolo[1,5-a]pyrimidin-3-yl]methanone | 25.0 | 50 |
| (3-methoxyphenyl)[7-(3-pyridinyl)pyrazolo[1,5-a]pyrimidin-3-yl]methanone | 25.0 | 75 |
| [4-(trifluoromethyl)phenyl][7-[4-(trifluoromethyl)phenyl]pyrazolo[1,5-a]pyrimidin-3-yl]methanone | 25.0 | 25 |
| (3-chlorophenyl)[7-(4-pyridinyl)pyrazolo[1,5-a]pyrimidin-3-yl]methanone | 25.0 | 50 |
| (3-chlorophenyl)[7-(3-pyridinyl)pyrazolo[1,5-a]pyrimidin-3-yl]methanone | 25.0 | 50 |
| [7-(3,4-dichlorophenyl)pyrazolo[1,5-a]pyrimidin-3-yl][4-(trifluoromethyl)phenyl]methanone | 25.0 | 50 |
| (4-fluorophenyl)[6-methyl-7-(3-pyridinyl)pyrazolo[1,5-a]pyrimidin-3-yl]methanone | 25.0 | 75 |
| (3-chlorophenyl)[7-(4-fluorophenyl)pyrazolo[1,5-a]pyrimidin-3-yl]methanone | 25.0 | 25 |
| (2,5-dichlorophenyl)[7-(4-fluorophenyl)pyrazolo[1,5-a]pyrimidin-3-yl]methanone | 25.0 | 25 |
| (2,5-dichlorophenyl)[7-(3-pyridinyl)pyrazolo[1,5-a]pyrimidin-3-yl]methanone | 25.0 | 25 |
| (2,5-dichlorophenyl)[7-(4-pyridinyl)pyrazolo[1,5-a]pyrimidin-3-yl]methanone | 25.0 | 25 |
| [7-[4-(methylthio)phenyl]pyrazolo[1,5-a]pyrimidin-3-yl]phenylmethanone | 25.0 | 50 |
| (2-methylphenyl)[7-(3-pyridinyl)pyrazolo[1,5-a]pyrimidin-3-yl]methanone | 25.0 | 25 |
| (2-methylphenyl)[7-(4-pyridinyl)pyrazolo[1,5-a]pyrimidin-3-yl]methanone | 25.0 | 25 |
| (2-chlorophenyl)[7-(4-pyridinyl)pyrazolo[1,5-a]pyrimidin-3-yl]methanone | 25.0 | 25 |
| (2-methylphenyl)[7-[4-(trifluoromethyl)phenyl]pyrazolo[1,5-a]pyrimidin-3-yl]methanone | 25.0 | 25 |
| 4-pyridinyl[7-(3-pyridinyl)pyrazolo[1,5-a]pyrimidin-3-yl]methanone | 25.0 | 100 |
| 4-pyridinyl[7-[3-(trifluoromethyl)phenyl]pyrazolo[1,5-a]pyrimidin-3-yl]methanone | 25.0 | 100 |
| [7-(4-fluorophenyl)pyrazolo[1,5-a]pyrimidin-3-yl]-4-pyridinylmethanone | 25.0 | 75 |
| 2-pyridinyl[7-[4-(trifluoromethyl)phenyl]pyrazolo[1,5-a]pyrimidin-3-yl]methanone | 25.0 | 25 |
| [4-(dimethylamino)phenyl][7-(3-pyridinyl)pyrazolo[1,5-a]pyrimidin-3-yl]methanone | 25.0 | 100 |
| [4-(dimethylamino)phenyl][7-(4-pyridinyl)pyrazolo[1,5-a]pyrimidin-3-yl]methanone | 25.0 | 75 |
| [4-(dimethylamino)phenyl][7-[3-(trifluoromethyl)phenyl]pyrazolo[1,5-a]pyrimidin-3-yl]methanone | 25.0 | 100 |
| [2-methyl-7-(4-pyridinyl)pyrazolo[1,5-a]pyrimidin-3-yl]phenylmethanone | 25.0 | 25 |
| [6-methyl-7-[3-(trifluoromethyl)phenyl]pyrazolo[1,5-a]pyrimidin-3-yl]phenylmethanone | 25.0 | 25 |
| (2-methoxyphenyl)[7-(3-pyridinyl)pyrazolo[1,5-a]pyrimidin-3-yl]methanone | 25.0 | 75 |
| 1,3-benzodioxol-5-yl[7-(3-pyridinyl)pyrazolo[1,5-a]pyrimidin-3-yl]methanone | 25.0 | 50 |
| 1,3-benzodioxol-5-yl[7-(4-pyridinyl)pyrazolo[1,5-a]pyrimidin-3-yl]methanone | 25.0 | 25 |
| (4-ethoxyphenyl)[7-(3-pyridinyl)pyrazolo[1,5-a]pyrimidin-3-yl]methanone | 25.0 | 25 |
| 2-naphthalenyl[7-(3-pyridinyl)pyrazolo[1,5-a]pyrimidin-3-yl]methanone | 25.0 | 25 |
| 2-thienyl[7-[4-(trifluoromethyl)phenyl]pyrazolo[1,5-a]pyrimidin-3-yl]methanone | 25.0 | 25 |
| [7-(3-fluorophenyl)pyrazolo[1,5-a]pyrimidin-3-yl]-2-thienylmethanone | 25.0 | 25 |
| [7-(4-fluorophenyl)pyrazolo[1,5-a]pyrimidin-3-yl](2-methoxyphenyl)methanone | 25.0 | 50 |
| (5-methyl-2-thienyl)[7-(3-pyridinyl)pyrazolo[1,5-a]pyrimidin-3-yl]methanone | 25.0 | 25 |
| 3-thienyl[7-[3-(trifluoromethyl)phenyl]pyrazolo[1,5-a]pyrimidin-3-yl]methanone | 25.0 | 75 |
| [7-(3-pyridinyl)pyrazolo[1,5-a]pyrimidin-3-yl]-3-thienylmethanone | 25.0 | 50 |
| (4-ethylphenyl)[7-(3-pyridinyl)pyrazolo[1,5-a]pyrimidin-3-yl]methanone | 25.0 | 100 |
| [7-(4-pyridinyl)pyrazolo[1,5-a]pyrimidin-3-yl]-3-thienylmethanone | 25.0 | 50 |
| (2-fluorophenyl)[7-(4-pyridinyl)pyrazolo[1,5-a]pyrimidin-3-yl]methanone | 25.0 | 50 |
| (2-fluorophenyl)[7-(3-pyridinyl)pyrazolo[1,5-a]pyrimidin-3-yl]methanone | 25.0 | 100 |
| (2-fluorophenyl)[7-[3-(trifluoromethyl)phenyl]pyrazolo[1,5-a]pyrimidin-3-yl]methanone | 25.0 | 50 |
| phenyl[7-(3-pyridinyl)pyrazolo[1,5-a]pyrimidin-3-yl]methanone, pyridine-1-oxide | 25.0 | 25 |
| (4-methoxyphenyl)[7-(3-pyridinyl)pyrazolo[1,5-a]pyrimidin-3-yl]methanone, pyridine-1-oxide | 25.0 | 25 |
| [7-[3-(ethylamino)phenyl]pyrazolo[1,5-a]pyrimidin-3-yl]-2-furanylmethanone | 25.0 | 100 |
| [7-[3-(ethylamino)phenyl]pyrazolo[1,5-a]pyrimidin-3-yl]phenylmethanone | 25.0 | 100 |
| N—[3-[3-(2-furanylcarbonyl)pyrazolo[1,5-a]pyrimidin-7-yl]phenyl]-N—methylpropanamide | 6.0 | 100 |
| N—[3-(3-benzoylpyrazolo[1,5-a]pyrimidin-7-yl)phenyl]-N—methylpropanamide | 0.8 | 100 |
| N—[3-[3-(2-furanylcarbonyl)pyrazolo[1,5-a]pyrimidin-7-yl]phenyl]-N—methylacetamide | 25.0 | 100 |
| N—[3-(3-benzoylpyrazolo[1,5-a]pyrimidin-7-yl)phenyl]-N—methylacetamide | 0.8 | 75 |
| N—[3-(3-benzoylpyrazolo[1,5-a]pyrimidin-7-yl)phenyl]-N—ethylpropanamide | 12.5 | 100 |
| N—ethyl-N—[3-[3-(2-furanylcarbonyl)pyrazolo[1,5-a]pyrimidin-7-yl]phenyl]acetamide | 12.5 | 100 |
| N—[3-(3-benzoylpyrazolo[1,5-a]pyrimidin-7-yl)phenyl]-N—ethylacetamide | 6.2 | 100 |

Another test which has been used to assess antianxiety effects is a nonconditioned passive avoidance procedure described by [J. R. Vogel, B. Beer and D. E. Clody, "A Simple and Reliable Conflict Procedure for Testing Anti-Anxiety Agents", Psychopharmacologia, 21, 1–7 (1971)]. A conflict situation is induced in rats by a modification of this method.

Groups of 6 naive, Wistar strain rats, weighing 200–240 g each were deprived of water for 48 hours and food for 24 hours. The test compounds were administered in single or graded, oral or intraperitoneal doses, suspended in a 2% starch vehicle containing 0.5% v/v polyethylene glycol and one drop of polysorbate 80. Control animals received the vehicle alone. At 30 to 60 minutes each rat was placed in an individual plexiglass chamber. Water was available ad libitum from a tap located in the rear of the chamber. A 0.7 milliampere DC shocking current was established between the stainless steel grid floor and the tap. After 20 licks of non-shocked drinking, a shock was delivered for 2 seconds and then further shocks were delivered on a ratio of one shock for 2 seconds for every 20 licks. This was continued for a total of 3 minutes. The number of shocks taken by each rat during the 3 minute interval was recorded and compared to a control group. The test compounds are considered active if the number of shocks received by the test group is significantly higher than the control group by the Mann-Witney U test. Results of this test on representative compounds of this invention appear in Table II.

TABLE II

Noncontitioned Passive Avoidance Test in Rats

| Compound | Dose mg/kg | Result |
|---|---|---|
| phenyl[7-(3-pyridinyl)pyrazolo[1,5-a]pyrimidin-3-yl]methanone | 25.0 | Active |
| (4-fluorophenyl)[7-(4-pyridinyl)pyrazolo[1,5-a]pyrimidin-3-yl]methanone | 25.0 | Active |
| phenyl[7-(4-pyridinyl)pyrazolo[1,5-a]pyrimidin-3-yl]methanone | 25.0 | Active |
| phenyl[7-[3-(trifluoromethyl)phenyl)pyrazolo[1,5-a]pyrimidin-3-yl]methanone | 25.0 | Active |
| (4-fluorophenyl)[7-[3-(trifluoromethyl)phenyl]pyrazolo[1,5-a]pyrimidin-3-yl]methanone | 25.0 | Active |
| (4-fluorophenyl)[7-(3-pyridinyl)pyrazolo[1,5-a]pyrimidin-3-yl]methanone | 25.0 | Active |
| [7-(3-pyridinyl)pyrazolo[1,5-a]pyrimidin-3-yl][3-(trifluoromethyl)phenyl]methanone | 25.0 | Active |
| 2-thienyl[7-[3-(trifluoromethyl)phenyl]pyrazolo[1,5-a]pyrimidin-3-yl]methanone | 25.0 | Active |
| 2-furanyl[7-(4-pyridinyl)pyrazolo[1,5-a]pyrimidin-3-yl]methanone | 25.0 | Active |
| 2-furanyl[7-[3-(trifluoromethyl)phenyl]pyrazolo[1,5-a]pyrimidin-3-yl]methanone | 25.0 | Active |
| 2-furanyl[7-(3-pyridinyl)pyrazolo[1,5-a]pyrimidin-3-yl]methanone | 25.0 | Active |
| 4-pyridinyl[7-(4-pyridinyl)pyrazolo[1,5-a]pyrimidin-3-yl]methanone | 25.0 | Active |
| 4-methylphenyl)[7-(3-pyridinyl)pyrazolo[1,5-a]pyrimidin-3-yl]methanone | 25.0 | Active |
| 4-methylphenyl)[7-[3-(trifluoromethyl)phenyl]pyrazolo[1,5-a]pyrimidin-3-yl]methanone | 12.5 | Active |
| phenyl[7-(4-pyridinyl)pyrazolo[1,5-a]pyrimidin-3-yl]methanone, pyridine-1-oxide | 25.0 | Active |
| 2-pyridinyl[7-(3-pyridinyl)pyrazolo[1,5-a]pyrimidin-3-yl]methanone | 25.0 | Active |
| 2-pyridinyl[7-[3-(trifluoromethyl)phenyl]pyrazolo[1,5-a]pyrimidin-3-yl]methanone | 25.0 | Active |
| 2-pyridinyl[7-(4-pyridinyl)pyrazolo[1,5-a]pyrimidin-3-yl]methanone | 25.0 | Active |
| 3-fluorophenyl)[7-(4-pyridinyl)pyrazolo[1,5-a]pyrimidin-3-yl]methanone | 25.0 | Active |
| [7-(4-fluorophenyl)pyrazolo[1,5-a]pyrimidin-3-yl]phenyl-methanone | 25.0 | Active |
| (3-fluorophenyl)[7-(3-pyridinyl)pyrazolo)[1,5-a]pyrimidin-3-yl]methanone | 25.0 | Active |
| (2-chlorophenyl)[7-(3-pyridinyl)pyrazolo[1,5-a]pyrimidin-3-yl]methanone | 25.0 | Active |
| [6-methyl-7-(4-pyridinyl)pyrazolo[1,5-a]pyrimidin-3-yl]phenyl-methanone | 25.0 | Active |
| 3-furanyl[7-(3-pyridinyl)pyrazolo[1,5-a]pyrimidin-3-yl]methanone | 25.0 | Active |
| 4-pyridinyl[7-(3-pyridinyl)pyrazolo[1,5-a]pyrimidin-3-yl]methanone | 25.0 | Active |
| (3-methoxyphenyl)[7-(3-pyridinyl)pyrazolo[1,5-a]pyrimidin-3-yl]methanone | 25.0 | Active |
| 4-pyridinyl[7-[3-(trifluoromethyl)phenyl]pyrazolo[1,5-a]pyrimidin-3-yl]methanone | 25.0 | Active |
| [4-(dimethylamino)phenyl][7-(3-pyridinyl)pyrazolo[1,5-a]pyrimidin-3-yl]methanone | 25.0 | Active |
| [4-(dimethylamino)phenyl][7-[3-(trifluoromethyl)phenyl]pyrazolo[1,5-a]pyrimidin-3-yl]methanone | 25.0 | Active |
| 1,3-benzodioxol-5-yl[7-(3-pyridinyl)pyrazolo[1,5-a]pyrimidin-3-yl]methanone | 25.0 | Active |
| [7-(3-pyridinyl)pyrazolo[1,5-a]pyrimidin-3-yl]-3-thienylmethanone | 25.0 | Active |
| (4-ethylphenyl)[7-(3-pyridinyl)pyrazolo[1,5-a]pyrimidin-3-yl]methanone | 25.0 | Active |
| (2-fluorophenyl)[7-(4-pyridinyl)pyrazolo[1,5-a]pyrimidin-3-yl]methanone | 25.0 | Active |
| (2-fluorophenyl)[7-(3-pyridinyl)pyrazolo[1,5-a]pyrimidin-3-yl]methanone | 25.0 | Active |
| (2-fluorophenyl)[7-[3-(trifluoromethyl)phenyl]pyrazolo[1,5-a]pyrimidin-3-yl]methanone | 25.0 | Active |
| [7-[3-(ethylamino)phenyl]pyrazolo[1,5-a]pyrimidin-3-yl]-2-furanylmethanone | 25.0 | Active |
| [7-[3-(ethylamino)phenyl]pyrazolo[1,5-a]pyrimidin-3-yl] phenylmethanone | 25.0 | Active |
| (3,4-dimethoxyphenyl)[7-(3-pyridinyl)pyrazolo[1,5-a]pyrimidin-3-yl]methanone | 25.0 | Active |
| (3-methylphenyl)[7-(3-pyridinyl)pyrazolo[1,5-a]pyrimidin-3-yl]methanone | 25.0 | Active |
| (4-chlorophenyl)[7-[3-(trifluoromethyl)phenyl]pyrazolo[1,5-a]pyrimidin-3-yl]methanone | 25.0 | Active |
| [7-(4-fluorophenyl)pyrazolo[1,5-a]pyrimidin-3-yl]-2-pyridinyl-methanone | 25.0 | Active |
| (4-fluorophenyl)[7-(4-fluorophenyl)pyrazolo[1,5-a]pyrimidin-3-yl]methanone | 25.0 | Active |
| (4-methoxyphenyl)[7-(3-pyridinyl)pyrazolo[1,5-a]pyrimidin-3-yl]methanone | 12.5 | Active |
| N—[3-[3-(2-furanylcarbonyl)pyrazolo[1,5-a]pyrimidin-7-yl]phenyl]-N—methylpropanamide | 25.0 | Active |
| N—ethyl-N—[3-[3-(2-furanylcarbonyl)pyrazolo[1,5-a]pyrimidin-7-yl]phenyl]propanamide | 12.5 | Active |
| N—[4-(3-benzoylpyrazolo[1,5-a]pyrimidin-7-yl)phenyl]-N—methylacetamide | 25.0 | Active |
| N—[3-(3-benzoylpyrazolo[1,5-a]pyrimidin-7-yl)phenyl]-N—methylpropanamide | 1.5 | Active |
| N—[3-[3-(2-furanylcarbonyl)pyrazolo[1,5-a]pyrimidin-7-yl]phenyl]-N—methylacetamide | 25.0 | Active |
| N—[3-(3-benzoylpyrazolo[1,5-a]pyrimidin-7-yl)phenyl]-N—methylacetamide | 3.1 | Active |
| N—[3-(3-benzoylpyrazolo[1,5-a]pyrimidin-7-yl)phenyl]-N—ethylpropanamide | 12.5 | Active |
| N—ethyl-N—[3-[3-(2-furanylcarbonyl)pyrazolo[1,5-a]pyrimidin-7-yl]phenyl]acetamide | 12.5 | Active |
| N—[3-(3-benzoylpyrazolo[1,5-a]pyrimidin-7-yl)phenyl]-N—ethylacetamide | 25.0 | Active |

Another test utilized for the determination of anxiolytic activity is the measurement of the ability of test compounds to inhibit the binding of tritiated benzodiazepines to brain-specific receptors of warm-blooded animals. A modification of the method described by R. F. Squires, et al., Nature, 266, No. 21, p 732 (April, 1977) and H. Mohler, et al., Science, 198, p 849 (1977) was employed.

Male albino rats (Wistar strain, weighing 150-200 g each) were obtained from Royalhart Farms. $^3$H-Methyldiazepam (79.9 Ci/mmol) and $^3$H-methyl-flunitrazepam (84.3 Ci/mmol) were obtained from New England Nuclear. The test compounds were solubilized in either dimethylformamide, acetic acid, ethanol or hydrochloric acid.

Whole cortex of rats was homogenized gently in 20 volumes of ice-cold 0.32M sucrose, centrifuged twice at 1000 g for 10 minutes and then recentrifuged at 30,000 g for 20 minutes to produce a crude $P_2$-synaptosomal fraction. The $P_2$-fraction was either: (1) resuspended in twice the original volume in hypotonic 50 mM Tris.HCl (pH 7.4), or (2) resuspended in one-half the original volume in hypotonic 10 mM Tris.HCl (pH 7.4) and frozen ($-20°$ C.) until time of use. Frozen $P_2$ preparations were thawed and resuspended in four times the original homogenizing volume at time of assay.

The binding assay consisted of 300 µl of the $P_2$-fraction suspension (0.2–0.4 mg protein), 100 µl of test drug and 100 µl of $^3$H-diazepam (1.5 nM, final concentration) or $^3$H-flunitrazepam (1.0 nM, final concentration) which was added to 1.5 ml of 50 mM Tris.HCl (pH 7.4). Nonspecific binding controls and total binding controls received 100 µl of diazepam (3 µM, final concentration) and 100 µl of deionized water, respectively, in place of the test compound. Incubation for 30 minutes proceeded in ice and was terminated by filtration, under vacuum, through Whatman GF/C glass fiber filters. The filters were washed twice with 5 ml of ice-cold 50 mM Tris.HCl (pH 7.4) and placed in scintillation vials. After drying at 50°–60° C. for 30 minutes, 10 ml of Beckman Ready-Solv ™ HP (a high performance premix scintillation cocktail, registered trademark of Beckman Instruments, Inc., Irvine, Calif. 92713) was added and the radioactivity determined in a scintillation counter.

Inhibition of binding was calculated by the difference between total binding and binding in the presence of test compound, divided by the total binding, X 100.

The results of this test on representative compounds of the present invention are given in Table III.

TABLE III

Inhibition of the Binding of $^3$H—Benzodiazepine to Brain-Specific Receptors of Rats

| Compound | % Inhibition |
| --- | --- |
| phenyl[7-(3-pyridinyl)pyrazolo[1,5-a]pyrimidin-3-yl]methanone | 45 |
| phenyl(7-phenylpyrazolo[1,5-a]pyrimidin-3-yl)methanone | 55 |
| phenyl[7-[3-(trifluoromethyl)phenyl]pyrazolo[1,5-a]pyrimidin-3-yl]methanone | 93 |
| (4-fluorophenyl)[7-[3-(trifluoromethyl)phenyl]pyrazolo[1,5-a]pyrimidin-3-yl]methanone | 50 |
| (4-fluorophenyl)(7-phenylpyrazolo[1,5-a]pyrimidin-3-yl)methanone | 42 |
| [7-(3,4-dimethoxyphenyl)-5-methylpyrazolo[1,5-a]pyrimidin-3-yl](4-fluorophenyl)methanone | 48 |
| [3-(trifluoromethyl)phenyl][7-[3-(trifluoromethyl)phenyl]pyrazolo[1,5-a]pyrimidin-3-yl]methanone | 56 |
| [7-(3-pyridinyl)pyrazolo[1,5-a]pyrimidin-3-yl][3-(trifluoromethyl)phenyl]methanone | 38 |
| [5-methyl-7-(3-pyridinyl)pyrazolo[1,5-a]pyrimidin-3-yl]phenyl-methanone | 15 |
| phenyl[7-(3,4,5-trimethoxyphenyl)pyrazolo[1,5-a]pyrimidin-3-yl]methanone | 24 |
| 2-thienyl[7-[3-(trifluoromethyl)phenyl]pyrazolo[1,5-a]pyrimidin-3-yl]methanone | 99 |
| 2-furanyl[7-(4-pyridinyl)pyrazolo[1,5-a]pyrimidin-3-yl]methanone | 19 |
| (7-phenylpyrazolo[1,5-a]pyrimidin-3-yl)-[3-(trifluoromethyl)phenyl]methanone | 19 |
| [7-(3-pyridinyl)pyrazolo[1,5-a]pyrimidin-3-yl]-2-thienyl-methanone | 82 |
| [7-(2-furanyl)pyrazolo[1,5-a]pyrimidin-3-yl][3-(trifluoromethyl)phenyl]methanone | 36 |
| 2-furanyl[7-[3-(trifluoromethyl)phenyl]pyrazolo[1,5-a]pyrimidin-3-yl]methanone | 98 |
| 2-furanyl[7-(3-pyridinyl)pyrazolo[1,5-a]pyrimidin-3-yl]methanone | 72 |
| [7-(2-fluorophenyl)pyrazolo[1,5-a]pyrimidin-3-yl]-2-furanyl-methanone | 34 |
| 2-furanyl(7-phenylpyrazolo[1,5-a]pyrimidin-3-yl)methanone | 81 |
| [2-methyl-7-(3-pyridinyl)pyrazolo[1,5-a]pyrimidin-3-yl]phenyl-methanone | 52 |
| [7-(4-pyridinyl)pyrazolo[1,5-a]pyrimidin-3-yl][3-(trifluoromethyl)phenyl]methanone | 99 |
| 4-pyridinyl[7-(4-pyridinyl)pyrazolo[1,5-a]pyrimidin-3-yl]methanone | 11 |
| (2-methyl-7-[3-(trifluoromethyl)phenyl]pyrazolo[1,5-a]pyrimidin-3-yl)phenyl-methanone | 54 |
| [7-(4-pyridinyl)pyrazolo[1,5-a]pyrimidin-3-yl]-2-thienyl-methanone | 62 |
| phenyl[7-(2-thienyl)pyrazolo[1,5-a]pyrimidin-3-yl]methanone | 96 |
| phenyl[7-(2-pyridinyl)pyrazolo[1,5-a]pyrimidin-3-yl]methanone | 30 |
| [7-(3-chlorophenyl)pyrazolo[1,5-a]pyrimidin-3-yl]phenyl-methanone | 95 |
| [5-methyl-7-(4-pyridinyl)pyrazolo[1,5-a]pyrimidin-3-yl]phenyl-methanone | 93 |
| [7-[2-chloro-5-(trifluoromethyl)phenyl]pyrazolo[1,5-a]pyrimidin-3-yl]phenyl-methanone | 86 |
| [7-(3-fluorophenyl)pyrazolo[1,5-a]pyrimidin-3-yl]phenyl-methanone | 88 |
| phenyl[7-(3-thienyl)pyrazolo[1,5-a]pyrimidin-3-yl]methanone | 96 |
| [7-[3-(methylthio)phenyl]pyrazolo[1,5-a]pyrimidin-3-yl]phenyl-methanone | 98 |
| [7-(3,4-dichlorophenyl)-5-methylpyrazolo[1,5-a]pyrimidin-3-yl]phenyl-methanone | 97 |
| (4-methylphenyl)[7-(3-pyridinyl)pyrazolo[1,5-a]pyrimidin-3-yl]methanone | 56 |
| (4-methylphenyl)[7-(2-pyridinyl)pyrazolo[1,5-a]pyrimidin-3-yl]methanone | 13 |
| (4-methylphenyl)[7-(4-pyridinyl)pyrazolo[1,5-a]pyrimidin-3-yl]methanone | 19 |
| (4-methylphenyl)[7-(3-thienyl)pyrazolo[1,5-a]pyrimidin-3-yl]methanone | 58 |
| phenyl[7-(4-pyridinyl)pyrazolo[1,5-a]pyrimidin-3-yl]methanone, pyridine-1-oxide | 39 |
| 2-pyridinyl[7-(3-pyridinyl)pyrazolo[1,5-a]pyrimidin-3-yl]methanone | 98 |
| 2-pyridinyl[7-(2-pyridinyl)pyrazolo[1,5-a]pyrimidin-3-yl]methanone | 77 |
| 2-pyridinyl[7-[3-(trifluoromethyl)phenyl]pyrazolo[1,5-a]pyrimidin-3-yl]methanone | 93 |
| 2-pyridinyl[7-(4-pyridinyl)pyrazolo[1,5-a]pyrimidin-3-yl]methanone | 29 |
| (4-fluorophenyl)[7-(4-pyridinyl)pyrazolo[1,5-a]pyrimidin-3-yl]methanone, pyridine-1-oxide | 15 |
| 2-pyridinyl[7-(2-thienyl)pyrazolo[1,5-a]pyrimidin-3-yl]methanone | 24 |
| [7-(2,5-dichlorophenyl)pyrazolo[1,5-a]pyrimidin-3-yl]phenyl-methanone | 21 |
| [7-(4-fluorophenyl)pyrazolo[1,5-a]pyrimidin-3-yl]phenyl-methanone | 18 |
| [7-(3,5-dichlorophenyl)pyrazolo[1,5-a]pyrimidin-3-yl]phenyl-methanone | 20 |
| (3-fluorophenyl)[7-(3-pyridinyl)pyrazolo- | 20 |

TABLE III-continued

Inhibition of the Binding of $^3$H—Benzodiazepine to Brain-Specific Receptors of Rats

| Compound | % Inhibition |
|---|---|
| [1,5-a]pyrimidin-3-yl]methanone | |
| (4-fluorophenyl)[7-(2-pyridinyl)pyrazolo-[1,5-a]pyrimidin-3-yl]methanone | 17 |
| (2-chlorophenyl)[7-(3-pyridinyl)pyrazolo-[1,5-a]pyrimidin-3-yl]methanone | 24 |
| (4-fluorophenyl)[5-methyl-7-(3-pyridinyl)-pyrazolo[1,5-a]pyrimidin-3-yl]methanone | 25 |
| (4-fluorophenyl)[7-(2-fluorophenyl)-pyrazolo[1,5-a]pyrimidin-3-yl]methanone | 22 |
| 4-(3-benzoylpyrazolo[1,5-a]pyrimidin-7-yl)benzonitrile | 10 |
| [5-methyl-7-[3-(trifluoromethyl)phenyl]-pyrazolo[1,5-a]pyrimidin-3-yl]phenyl-methanone | 27 |
| [6-methyl-7-(4-pyridinyl)pyrazolo[1,5-a]-pyrimidin-3-yl]phenyl-methanone | 56 |
| (6-methyl-7-phenylpyrazolo[1,5-a]pyrimidin-3-yl)phenyl-methanone | 24 |
| 3-furanyl[7-(3-pyridinyl)pyrazolo[1,5-a]-pyrimidin-3-yl]methanone | 77 |
| (3,4-dimethoxyphenyl)[7-(3-pyridinyl)-pyrazolo[1,5-a]pyrimidin-3-yl]methanone | 75 |
| (3,4-dimethoxyphenyl)[7-[3-(trifluoro-methyl)phenyl]pyrazolo[1,5-a]pyrimidin-3-yl]methanone | 94 |
| (3-methylphenyl)[7-(3-pyridinyl)pyrazolo-[1,5-a]pyrimidin-3-yl]methanone | 70 |
| (3,5-dimethoxyphenyl)[7-(3-pyridinyl)-pyrazolo[1,5-a]pyrimidin-3-yl]methanone | 30 |
| (3 methylphenyl)[7-[3-(trifluoromethyl)-phenyl]pyrazolo[1,5-a]pyrimidin-3-yl]-methanone | 67 |
| (3-methylphenyl)[7-(3-methylphenyl)-pyrazolo[1,5-a]pyrimidin-3-yl]methanone | 75 |
| (4-chlorophenyl)[ 7-[3-(trifluoromethyl)-phenyl]pyrazolo[1,5-a]pyrimidin-3-yl]-methanone | 81 |
| (4-chlorophenyl)[7-(3-pyridinyl)pyrazolo-[1,5-a]pyrimidin-3-yl]methanone | 87 |
| (4-chlorophenyl)[7-(4-fluorophenyl)-pyrazolo[1,5-a]pyrimidin-3-yl]methanone | 16 |
| (3-fluorophenyl)[7-[3-(trifluoromethyl)-phenyl]pyrazolo[1,5-a]pyrimidin-3-yl]-methanone | 96 |
| [5-methyl-7-(4-pyridinyl)pyrazolo[1,5-a]-pyrimidin-3-yl]phenyl-methanone, pyridine-1-oxide | 52 |
| (3-fluorophenyl)[7-(4-fluorophenyl)pyra-zolo[1,5-a]pyrimidin-3-yl]methanone | 52 |
| [7-(4-fluorophenyl)pyrazolo[1,5-a]-pyrimidin-3-yl]-2-pyridinyl-methanone | 64 |
| (4-fluorophenyl)[7-(4-fluorophenyl)-pyrazolo[1,5-a]pyrimidin-3-yl]methanone | 34 |
| N—[3-(3-benzoylpyrazolo[1,5-a]pyrimidin-7-yl)phenyl]acetamide | 65 |
| N—[4-(3-benzoylpyrazolo[1,5-a]pyrimidin-7-yl)phenyl]acetamide | 33 |

The sedative-hypnotic properties of the novel compounds of the instant invention have been established by their effect on the duration of ethanol induced narcosis in rats as a measurement of sedation. Groups of at least 8 rats were administered graded oral doses of the test compounds or vehicle 60 minutes prior to intraperitoneal treatment with 3.2 g/kg ethanol. Rats were then observed continuously for 180 minutes for the incidence and duration of ethanol induced narcosis. A rat was considered to exhibit narcosis if it remained in a supine position on a horizontal surface for at least 1 minute; the end of narcosis was defined as the rat spontaneously righting itself and remaining righted for at least 1 minute. The duration of narcosis was the total time the rat remained in a supine position. The MED [lowest dose necessary to cause a significant ($p \leq 0.05$, two-tailed Student's t test) increase in the duration of ethanol induced narcosis in rats] of representative compounds of this invention are shown in Table IV. Test compounds were dissolved or suspended in a 2% aqueous starch suspension containing 5% polyethyleneglycol 400 and a drop of Tween ®80; ethanol (95%) was adjusted to final concentration (V:V) with 0.85% saline. All treatments were administered in a constant volume of 5 ml/kg.

TABLE IV

Effects on the Duration of Ethanol Induced Narcosis in Rats

| Compound | MED (mg/kg) |
|---|---|
| phenyl[7-(3-pyridinyl)pyrazolo[1,5-a]-pyrimidin-3-yl]-methanone | 16 |
| (4-fluorophenyl)[7-(4-pyridinyl)-pyrazolo[1,5-a-]pyrimidin-3-yl]-methanone | 6 |
| phenyl[7-(4-pyridinyl)pyrazolo[1,5-a]-pyrimidin-3-yl]-methanone | 8 |
| 2-furanyl[7-[3-(trifluoromethyl)-phenyl]pyrazolo[1,5-a]pyrimidin-3-yl]-methanone | 32 |
| 2-furanyl[7-(3-pyridinyl)pyrazolo-[1,5-a]pyrimidin-3-yl]-methanone | 32 |
| (2-chlorophenyl)[7-(3-pyridinyl)-pyrazolo[1,5-a]pyrimidin-3-yl]-methanone | 4 |

The novel compounds of this invention have also been shown to have skeletal muscle relaxant activity by two tests. The first test measures the effect of representative compounds on the ability of rats to remain on an inclined screen. Groups of at least 6 rats were treated orally with graded doses of test compounds or vehicle and placed on a wire mesh screen (inclined at an angle of 60° from a horizontal level) 65 minutes later. The number of rats falling off the screen within 30 minutes was recorded. The $ED_{50}$(dose necessary to cause 50% of the animals tested to fall off) was calculated according to the linear arc-sine transformation method of Finney, D. J. Statistical Methods in Biological Assay, 2nd Ed., Hafner, N. Y., 1964, pp. 454 ff. Compounds were dissolved or suspended in a 2% aqueous starch suspension containing 5% polyethylene glycol 400 and a drop of polysorbate 80, and administered in a constant volume of 5 ml/kg. The results of representative compounds of this invention appear in Table V.

TABLE V

Effect on Ability of Rats to Remain on an Inclined Screen

| Compound | $ED_{50}$ (mg/kg) |
|---|---|
| phenyl[7-(3-pyridinyl)pyrazolo[1,5-a]-pyrimidin-3-yl]-methanone | 68.5 |
| (4-fluorophenyl)[7-(4-pyridinyl)pyrazolo-[1,5-a]pyrimidin-3-yl]-methanone | 98 |
| phenyl[7-(4-pyridinyl)pyrazolo[1,5-a]-pyrimidin-3-yl]-methanone | 9.9 |
| phenyl[7-[3-(trifluoromethyl)phenyl]-pyrazolo[1,5-a]pyrimidin-3-yl]-methanone | 5.5 |
| 2-furanyl[7-(3-pryidinyl)pyrazolo[1,5-a]-pyrimidin-3-yl]-methanone | 167 |
| (4-methylphenyl)[7-(3-pyridinyl)-pyrazolo-[1,5-a]pyrimidin-3-yl]-methanone | 11.1 |
| 2-pyridinyl[7-[3-(trifluoromethyl)-phenyl]pyrazolo[1,5-a]pyrimidin-3-yl]-methanone | 6.9 |
| (4-methoxyphenyl)[7-(3-pyridinyl)pyrazolo-[1,5-a]pyrimidin-3-yl]-methanone | 11.9 |

The second test to illustrate that the novel compounds of the present invention possess skeletal muscle relaxant properties is the effect of representative compounds on the locomotor activity in rats. Groups of 6 rats were treated orally with vehicle (5 ml/kg) or graded doses of the test compounds. Sixty minutes later, individual rats were placed in Actophotometers and locomotor activity was measured for 5 minutes after a brief (30 sec.) habituation period. Motor Activity Counts (number of crossings of the photo cells) were recorded for each rat, and mean activity counts were calculated for each treatment group. The dose causing a 50% decrease in mean activity counts compared with the vehicle group ($MDD_{50}$) was calculated from a linear regression equation. The test results of representative compounds appear in Table VI.

TABLE VI
Effects on Locomotor Activity in Rats

| Compound | $MDD_{50}$ (mg/kg P.O.) |
|---|---|
| phenyl[7-(3-pyridinyl)pyrazolo[1,5-a]-pyrimidin-3-yl]-methanone | 51.4 |
| (4-fluorophenyl)[7-(4-pyridinyl)pyrazolo-[1,5-a]pyrimidin-3-yl]-methanone | 48.9 |
| phenyl[7-(4-pyridinyl)pyrazolo[1,5-a]-pyrimidin-3-yl]-methanone | 21.2 |
| phenyl[7-[3-(trifluoromethyl)phenyl]-pyrazolo[1,5-a]pyrimidin-3-yl]-methanone | 5.5 |
| 2-furanyl[7-(3-pyridinyl)pyrazolo[1,5-a]-pyrimidin-3-yl]-methanone | 500 |
| (4-methylphenyl)[7-(3-pyridinyl)pyrazolo-[1,5-a]pyrimidin-3-yl]-methanone | 13.2 |
| 2-pyridinyl[7-[3-(trifluoromethyl)phenyl]-pyrazolo[1,5-a]pyrimidin-3-yl]-methanone | 7.0 |
| 2-pyridinyl[7-(4-pyridinyl)pyrazolo-[1,5-a]pyrimidin-3-yl]-methanone | 100.6 |
| (4-methoxyphenyl)[7-(3-pyridinyl)pyrazolo-[1,5-a]pyrimidin-3-yl]-methanone | 10.5 |

The novel compounds of the present invention have been found to be highly useful for drug therapy in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 10 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of nonvolatile, normally liquid, polyethylene glycols which are soluble in both water and organic liquids and which have molecular weight of from about 200 to 1500. Although the amount of active compound dissolved in the above vehicle may vary from 0.10% to 10.0% by weight, it is preferred that the amount of active compound employed be from about 3.0 to about 9.0% by weight. Although various mixtures of the aforementioned nonvolatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05 to about 0.2% concentrations of antioxidant are employed.

For intramuscular injection, the preferred concentration of active compound is 0.25 to 0.50 mg/ml of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food or the diet. For oral therapeutic administration, the active compounds may be incorporated with excipients and used in the form of tablets, troches, capsules, elixirs, suspensions, syrups, wafers, and the like. Additionally, the active ingredient may be incorporated with the proper pharmaceutical carrier or carriers known in the art to produce a sustained-release tablet or capsule. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain one or more of the following: A binder such as gum tragacanth, acacia, corn starch or gelatin; excipients such as dicalcium phosphate; a disintegrating agent such as corn starch, potato starch, alginic acid and the like; a lubricant such as magnesium stearate; a wetting agent such as sodium lauryl sulfate and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially nontoxic in the amounts employed.

The following non-limiting examples illustrate the preparation of representative compounds of the present invention.

EXAMPLE 1

Phenyl[7-(3-pyridinyl)pyrazolo[1,5-a]pyrimidin-3-yl]methanone

A reaction mixture of 1.87 g of (3-amino-1H-pyrazol-4-yl)phenyl-methanone and 1.76 g of 3-dimethylamino-1-(3-pyridinyl)-2-propen-1-one in 25 ml of glacial acetic acid was refluxed for 6 hours and then the solvent was removed in vacuo giving a crystalline residue. This residue was partitioned between saturated aqueous sodium bicarbonate and methylene chloride. The organic layer was dried with anhydrous sodium sulfate and then passed through a short pad of hydrous magnesium silicate. The addition of hexane to the refluxing eluate induced crystallization. After cooling, the desired product was collected, giving 2.45 g, mp 202°–203° C.

Following the general procedure of Example 1 and using appropriate substituted pyrazole derivatives and either appropriate substituted 3-dimethyl-1-(aryl)-2-propen(buten)-1-ones or in certain instances other aldehydes or ketones, the products of Examples 2–131, listed in Table VII, were obtained.

TABLE VII

| Ex. | Pyrazole | 3-Dimethylamino-1-(aryl)-2-propen-1-one | Product | MP °C. |
|---|---|---|---|---|
| 2 | (3-amino-1H—pyrazol-4-yl)(4-fluorophenyl)-methanone | 3-dimethylamino-1-(4-pyridinyl)-2-propen-1-one | (4-fluorophenyl) [7-(4-pyridinyl)pyrazolo[1,5-a]pyrimidin-3-yl]methanone | 214–216 |
| 3 | (3-amino-1H—pyrazol-4-yl)phenyl-methanone | 3-dimethylamino-1-(4-pyridinyl)-2-propen-1-one | phenyl[7-(4-pyridinyl)pyrazolo[1,5-a]pyrimidin-3-yl]methanone | 185–186 |
| 4 | (3-amino-1H—pyrazol-4-yl)phenyl-methanone | 3-dimethylamino-1-(phenyl)-2-propen-1-one | phenyl(7-phenylpyrazolo-[1,5-a]pyrimidin-3-yl)-methanone | 163–165 |
| 5 | (3-amino-1H—pyrazol-4-yl)phenyl-methanone | 3-dimethylamino-1-[3-(trifluoromethyl)phenyl]-2-propen-1-one | phenyl[7-[3-(trifluoromethyl)phenyl]pyrazolo[1,5-a]pyrimidin-3-yl]methanone | 148–150 |
| 6 | (3-amino-1H—pyrazol-4-yl)(4-fluorophenyl)-methanone | 3-dimethylamino-1-[3-(trifluoromethyl)phenyl]-2-propen-1-one | (4-fluorophenyl)[7-[3-(trifluoromethyl)phenyl]pyrazolo-[1,5-a]pyrimidin-3-yl]methanone | 176–177 |
| 7 | (3-amino-1H—pyrazol-4-yl)(4-fluorophenyl)-methanone | 3-dimethylamino-1-(3-pyridinyl)-2-propen-1-one | (4-fluorophenyl[7-(3-pyridinyl)pyrazolo[1,5-a]pyrimidin-3-yl]methanone | 235–236 |
| 8 | (3-amino-1H—pyrazol-4-yl)(4-fluorophenyl)-methanone | 3-dimethylamino-1-(phenyl)-2-propen-1-one | (4-fluorophenyl)(7-phenyl-pyrazolo[1,5-a]pyrimidin-3-yl]methanone | 166–168 |
| 9 | (3-amino-1H—pyrazol-4-yl)(4-fluorophenyl)-methanone | 1-(3,4-dimethoxyphenyl)-3-dimethylamino-2-buten-1-one | [7-(3,4-dimethoxyphenyl)-5-methylpyrazolo[1,5-a]pyrimidin-3-yl](4-fluorophenyl)-methanone | 197–199 |
| 10 | (3-amino-1H—pyrazol-4-yl)[3-(trifluoromethyl)-phenyl]methanone | 3-dimethylamino-1-[3-(trifluoromethyl)phenyl]-2-propen-1-one | [3-(trifluoromethyl)phenyl]-[7-[3-(trifluoromethyl)phenyl]pyrazolo[1,5-a]pyrimidin-3-yl]methanone | 157–159 |
| 11 | (3-amino-1H—pyrazol-4-yl)[3-(trifluoromethyl)-phenyl]methanone | 3-dimethylamino-1-(3-pyridinyl)-2-propen-1-one | [7-(3-pyridinyl)pyrazolo-[1,5-a]pyrimidin-3-yl][3-trifluoromethyl)phenyl]-methanone | 221–222 |
| 12 | (3-amino-1H—pyrazol-4-yl)phenyl-methanone | 3-dimethylamino-1-(3-pyridinyl)-2-buten-1-one | [5-methyl-7-(3-pyridinyl)-pyrazolo[1,5-a]pyrimidin-3-yl]phenyl-methanone | 196–198 |
| 13 | (3-amino-1H—pyrazol-4-yl)phenyl-methanone | 3-dimethylamino-1-(3,4,5-trimethoxyphenyl)-2-propen-1-one | phenyl[7-(3-4,5-trimethoxy-phenyl)pyrazolo[1,5-a]pyrimidin-3-yl]methanone | 162–164 |
| 14 | (3-amino-1H—pyrazol-4-yl)-2-thienyl-methanone | 3-dimethylamino-1-[3-(trifluoromethyl)phenyl]-2-propen-1-one | 2-thienyl[7-[3-(trifluoromethyl)phenyl]pyrazolo-[1,5-a]pyrimidin-3-yl]-methanone | 140–141 |
| 15 | (3-amino-1H—pyrazol-4-yl)-2-furanyl-methanone | 3-dimethylamino-1-(4-pyridinyl)-2-propen-1-one | 2-furanyl[7-(4-pyridinyl)-pyrazolo[1,5-a]pyrimidin-3-yl]methanone | 277–278 |
| 16 | (3-amino-1H—pyrazol-4-yl)[3-(trifluoromethyl)-phenyl]methanone | 3-dimethylamino-1-(phenyl)-2-propen-1-one | (7-phenylpyrazolo[1,5-a]-pyrimidin-3-yl)[3-(trifluoromethyl)phenyl]methanone | 188–190 |
| 17 | (3-amino-1H—pyrazol-4-yl)-2-thienyl-methanone | 3-dimethylamino-1-(3-pyridinyl)-2-propen-1-one | [7-(3-pyridinyl)pyrazolo-[1,5-a]pyrimidin-3-yl]-2-thienyl-methanone | 233–234 |
| 18 | (3-amino-1H—pyrazol-4-yl)[3-(trifluoromethyl)-phenyl]methanone | 3-dimethylamino-1-(2-furanyl)-2-propen-1-one | [7-(2-furanyl)pyrazolo-[1,5-a]pyrimidin-3-yl][3-(trifluoromethyl)phenyl]-methanone | 143–145 |
| 19 | (3-amino-1H—pyrazol-4-yl)-2-furanyl-methanone | 3-dimethylamino-1-[3-(trifluoromethyl)phenyl]-2-propen-1-one | 2-furanyl[7-[3-(trifluoromethyl)phenyl]pyrazolo[1,5-]-pyrimidin-3-yl]methanone | 153–155 |
| 20 | (3-amino-1H—pyrazol-4-yl)-2-furanyl-methanone | 3-dimethylamino-1-(3-pyridinyl)-2-propen-1-one | 2-furanyl[7-(3-pyridinyl)-pyrazolo[1,5-a]pyrimidin-3-yl]methanone | 228–229 |
| 21 | (3-amino-1H—pyrazol-4- | 3-dimethylamino-1-(2- | [7-(2-fluorophenyl)pyrazolo- | 180–181 |

TABLE VII-continued

| Ex. | Pyrazole | 3-Dimethylamino-1-(aryl)-2-propen-1-one | Product | MP °C. |
|---|---|---|---|---|
| | yl)-2-furanyl-methanone | fluorophenyl)-2-propen-1-one | [1,5-a]pyrimidin-3-yl]-2-furanyl-methanone | |
| 22 | (3-amino-1H—pyrazol-4-yl)-2-furanyl-methanone | 3-dimethylamino-1-(phenyl)-2-propen-1-one | 2-furanyl(7-phenylpyrazolo[1,5-a]pyrimidin-3-yl]-methanone | 179–180 |
| 23 | (3-amino-5-methyl-1H—pyrazol-4-yl)phenyl-methanone | 3-dimethylamino-1-(3-pyridyl)-2-propen-1-one | [2-methyl-7-(3-pyridinyl)-pyrazolo[1,5-a]pyrimidin-3-yl]phenyl-methanone | 193–195 |
| 24 | (3-amino-1H—pyrazol-4-yl)[3-(trifluoromethyl)-phenyl]methanone | 3-dimethylamino-1-(4-pyridinyl)-2-propen-1-one | [7-(4-pyridinyl)pyrazolo-[1,5-a]pyrimidin-3-yl][3-(trifluoromethyl)phenyl]methanone | 207–208 |
| 25 | (3-amino-1H—pyrazol-4-yl)-4-pyridinyl-methanone | 3-dimethylamino-1-(4-pyridinyl)-2-propen-1-one | 4-pyridinyl[7-(4-pyridinyl)-pyrazolo[1,5-a]pyrimidin-3-yl]methanone | 260–262 |
| 26 | (3-amino-5-methyl-1H—pyrazol-4-yl)phenyl-methanone | 3-dimethylamino-1-[3-(trifluoromethyl)-phenyl]-2-propen-1-one | (2-methyl-7-[3-(trifluoromethyl)phenyl]pyrazolo[1,5-a]pyrimidin-3-yl)phenyl-methanone | 156–158 |
| 27 | (3-amino-1H—pyrazol-4-yl)-2-thienyl-methanone | 3-dimethylamino-1-(4-pyridinyl)-2-propen-1-one | 7-(4-pyridinyl)pyrazolo-[1,5-a]pyrimidin-3-yl]-2-thienyl-methanone | 248–249 |
| 28 | (3-amino-1H—pyrazol-4-yl)[3-(trifluoromethyl)-phenyl]methanone | 3-dimethylamino-1-(3-chlorophenyl)-2-propen-1-one | [7-(3-chlorophenyl)pyrazolo-[1,5-a]pyrimidin-3-yl][3-(trifluoromethyl)phenyl]methanone | 178–180 |
| 29 | (3-amino-1H—pyrazol-4-yl)phenyl-methanone | 3-dimethylamino-1-(2-thienyl)-2-propen-1-one | phenyl[7-(2-thienyl)pyrazolo[1,5-a]pyrimidin-3-yl]methanone | 180–181 |
| 30 | (3-amino-1H—pyrazol-4-yl)phenyl-methanone | 3-dimethylamino-1-(2-pyridinyl)-2-propen-1-one | phenyl[7-(2-pyridinyl)pyrazolo[1,5-a]pyrimidin-3-yl]-methanone | 208–210 |
| 31 | (3-amino-1H—pyrazol-4-yl)phenyl-methanone | 3-dimethylamino-1-(3-chlorophenyl)-2-propen-1-one | [7-(3-chlorophenyl)pyrazolo-[1,5-a]pyrimidin-3-yl]phenyl-methanone | 136–138 |
| 32 | (3-amino-1H—pyrazol-4-yl)phenyl-methanone | 3-dimethylamino-1-(4-pyridinyl)-2-buten-1-one | [5-methyl-7-(4-pyridinyl)-pyrazolo[1,5-a]pyrimidin-3-yl]phenyl-methanone | 209–210 |
| 33 | (3-amino-1H—pyrazol-4-yl)phenyl-methanone | 3-dimethylamino-1-[2-chloro-5-(trifluoromethyl)phenyl]-2-propen-1-one | [7-[2-chloro-5-(trifluoromethyl)phenyl]pyrazolo-[1,5-a]pyrimidin-3-yl]phenyl-methanone | 145–147 |
| 34 | (3-amino-1H—pyrazol-4-yl)phenyl-methanone | 3-dimethylamino-1-(3-fluorophenyl)-2-propen-1-one | [7-(3-fluorophenyl)pyrazolo-[1,5-a]pyrimidin-3-yl]phenyl-methanone | 199–201 |
| 35 | (3-amino-1H—pyrazol-4-yl)phenyl-methanone | 3-dimethylamino-1-(3-thienyl)-2-propen-1-one | phenyl[7-(3-thienyl)pyrazolo[1,5-a]pyrimidin-3-yl]methanone | 150–152 |
| 36 | (3-amino-1H—pyrazol-4-yl)phenyl-methanone | 3-dimethylamino-1-[3-(methylthio)phenyl]-2-propen-1-one | [7-[3-(methylthio)phenyl]-pyrazolo[1,5-a]pyrimidin-3-yl]phenyl-methanone | 126–127 |
| 37 | (3-amino-1H—pyrazol-4-yl)phenyl-methanone | 1-(3,4-dichlorophenyl)-3-(dimethylamino)-2-buten-1-one | [7-(3,4-dichlorophenyl)-5-methylpyrazolo[1,5-a]pyrimidin-3-yl]phenyl-methanone | 194–196 |
| 38 | (3-amino-1H—pyrazol-4-yl)(4-methylphenyl)-methanone | 3-dimethylamino-1-(3-pyridinyl)-2-propen-1-one | (4-methylphenyl)[7-(3-pyridinyl)pyrazolo[1,5-a]pyrimidin-3-yl]methanone | 203–204 |
| 39 | (3-amino-1H—pyrazol-4-yl)(4-methylphenyl)-methanone | 3-dimethylamino-1-(2-pyridinyl)-2-propen-1-one | (4-methylphenyl)[7-(2-pyridinyl)pyrazolo[1,5-a]pyrimidin-3-yl]methanone | 188–189 |
| 40 | (3-amino-1H—pyrazol-4-yl)(4-methylphenyl)-methanone | 3-dimethylamino-1-(4-pyridinyl)-2-propen-1-one | (4-methylphenyl)[7-(4-pyridinyl)pyrazolo[1,5-a]pyrimidin-3-yl]methanone | 196–197 |
| 41 | (3-amino-1H—pyrazol-4-yl)(4-methylphenyl)-methanone | 3-dimethylamino-1-[3-(trifluoromethyl)-phenyl]-2-propen-1-one | (4-methylphenyl)[7-[3-(trifluoromethyl)phenyl]pyrazolo[1,5-a]pyrimidin-3-yl]-methanone | 158–159 |
| 42 | (3-amino-1H—pyrazol-4-yl)(4-methylphenyl)-methanone | 3-dimethylamino-1-(3-thienyl)-2-propen-1-one | (4-methylphenyl)[7-(3-thienyl)pyrazolo[1,5-a]-pyrimidin-3-yl]methanone | 168–169 |
| 43 | (3-amino-1H—pyrazol-4-yl)-2-pyridinyl-methanone | 3-dimethylamino-1-(3-pyridinyl)-2-propen-1-one | 2-pyridinyl[7-(3-pyridinyl)pyrazolo[1,5-a]pyrimidin-3-yl]methanone | 216–218 |
| 44 | (3-amino-1H—pyrazol-4-yl)-2-pyridinyl-methanone | 3-dimethylamino-1-(2-pyridinyl)-2-propen-1-one | 2-pyridinyl[7-(2-pyridinyl)pyrazolo[1,5-a]pyrimidin-3-yl]methanone | 158–160 |
| 45 | (3-amino-1H-pyrazol-4-yl)-2-pyridinyl-methanone | 3-dimethylamino-1-[3-(trifluoromethyl)phenyl]-2-propen-1-one | 2-pyridinyl[7-[3-(trifluoromethyl)phenyl]pyrazolo-[1,5-a]pyrimidin-3-yl]methanone | 166–167 |

TABLE VII-continued

| Ex. | Pyrazole | 3-Dimethylamino-1-(aryl)-2-propen-1-one | Product | MP °C. |
|---|---|---|---|---|
| 46 | (3-amino-1H—pyrazol-4-yl)-2-pyridinyl-methanone | 3-dimethylamino-1-(4-pyridinyl)-2-propen-1-one | 2-pyridinyl[7-(4-pyridinyl)-pyrazolo[1,5-a]pyrimidin-3-yl]methanone | 230–232 |
| 47 | (3-amino-1H—pyrazol-4-yl)-3-fluorophenyl-methanone | 3-dimethylamino-1-(4-pyridinyl)-2-propen-1-one | (3-fluorophenyl)[7-(4-pyridinyl)pyrazolo[1,5-a]pyrimidin-3-yl]methanone | 195–196 |
| 48 | (3-amino-1H—pyrazol-4-yl)-2-pyridinyl-methanone | 3-dimethylamino-1-(2-thienyl)-2-propen-1-one | 2-pyridinyl[7-(2-thienyl)-pyrazolo[1,5-a]pyrimidin-3-yl]methanone | 159–160 |
| 49 | (3-amino-1H—pyrazol-4-yl)phenyl-methanone | 3-dimethylamino-1-(2,5-dichlorophenyl)-2-propen-1-one | [7-(2,5-dichlorophenyl)pyrazolo[1,5-a]pyrimidin-3-yl]-phenyl-methanone | 194–195 |
| 50 | (3-amino-1H—pyrazol-4-yl)phenyl-methanone | 3-dimethylamino-1-(4-fluorophenyl)-2-propen-1-one | [7-(4-fluorophenyl)pyrazolo[1,5-a]pyrimidin-3-yl]phenyl-methanone | 187–188 |
| 51 | (3-amino-1H—pyrazol-4-yl)phenyl-methanone | 3-dimethylamino-1-(3,5-dichlorophenyl)-2-propen-1-one | [7-(3,5-dichlorophenyl)pyrazolo[1,5-a]pyrimidin-3-yl]-phenyl-methanone | 206–208 |
| 52 | (3-amino-1H—pyrazol-4-yl)-3-fluorophenyl-methanone | 3-dimethylamino-1-(3-pyridinyl)-2-propen-1-one | (3-fluorophenyl)[7-(3-pyridinyl)pyrazolo[1,5-a]pyrimidin-3-yl]methanone | 185–186 |
| 53 | (3-amino-1H—pyrazol-4-yl)(4-fluorophenyl)-methanone | 3-dimethylamino-1-(2-pyridinyl)-2-propen-1-one | (4-fluorophenyl)[7-(2-pyridinyl)pyrazolo[1,5-a]pyrimidin-3-yl]methanone | 213–215 |
| 54 | (3-amino-1H—pyrazol-4-yl)(2-chlorophenyl)-methanone | 3-dimethylamino-1-(3-pyridinyl)-2-propen-1-one | (2-chlorophenyl)[7-(3-pyridinyl)pyrazolo[1,5-a]pyrimidin-3-yl]methanone | 143–144 |
| 55 | (3-amino-1H—pyrazol-4-yl)(4-fluorophenyl)-methanone | 3-dimethylamino-1-(3-pyridinyl)-2-buten-1-one | (4-fluorophenyl)[5-methyl-7-(3-pyridinyl)yrazolo[1,5-a]-pyrimidin-3-yl]methanone | 256–257 |
| 56 | (3-amino-1H—pyrazol-4-yl)(4-fluorophenyl)-methanone | 3-dimethylamino-1-(2-fluorophenyl)-2-propen-1-one | (4-fluorophenyl)[7-(2-fluorophenyl)pyrazolo[1,5-a]pyrimidin-3-yl]methanone | 176–177 |
| 57 | (3-amino-1H—pyrazol-4-yl)(4-fluorophenyl)-methanone | 3-dimethylamino-1-[3-(trifluoromelthyl)-phenyl]-2-buten-1-one | (4-fluorophenyl)[5-methyl-7-[3-(trifluoromethyl)phenyl]pyrazolo[1,5-a]pyrimidin-3-yl]methanone | 189–190 |
| 58 | (3-amino-1H—pyrazol-4-yl)(4-fluorophenyl)-methanone | 3-dimethylamino-1-[4-(trifluoromethyl)phenyl]-2-propen-1-one | (4-fluorophenyl)[7-[4-(trifluoromethyl)phenyl]pyrazolo[1,5-a]pyrimidin-3-yl]methanone | 187–188 |
| 59 | (3-amino-1H—pyrazol-4-yl)(4-fluorophenyl)-methanone | 3-dimethylamino-1-(4-cyanophenyl)-2-propen-1-one | 4-[3-(4-fluorobenzoyl)pyrazolo[1,5-a]pyrimidin-7-yl]-benzonitrile | 264–266 |
| 60 | (3-amino-1H—pyrazol-4-yl)phenyl-methanone | 3-dimethylamino-1-(4-cyanophenyl)-2-propen-1-one | 4-(3-benzoylpyrazolo[1,5-a]-pyrimidin-7-yl)benzonitrile | 210–212 |
| 61 | (3-amino-1H—pyrazol-4-yl)phenyl-methanone | 3-dimethylamino-1-[3-(trifluoromethyl)-phenyl]-2-buten-1-one | [5-methyl-7-[3-(trifluoromethyl)phenyl]pyrazolo[1,5-a]pyrimidin-3-yl]-phenyl-methanone | 153–154 |
| 62 | (3-amino-1H—pyrazol-4-yl)(3,4,5-trimethoxyphenyl)methanone | 3-dimethylamino-1-(4-pyridinyl)-2-propen-1-one | [7-(4-pyridinyl)pyrazolo-[1,5-a]pyrimidin-3-yl]-[3,4,5-trimethoxyphenyl]-methanone | 210–211 |
| 63 | (3-amino-1H—pyrazol-4-yl)phenyl-methanone | 3-dimethylamino-2-methyl-1-(4-pyridinyl)-2-propen-1-one | [6-methyl-7-(4-pyridinyl)-pyrazolo[1,5-a]pyrimidin-3-yl]phenyl-methanone | 210–211 |
| 64 | (3-amino-1H—pyrazol-4-yl)phenyl-methanone | 3-dimethylamino-2-methyl-1-phenyl-2-propen-1-one | (6-methyl-7-phenylpyrazolo-[1,5-a]pyrimidin-3-yl)phenyl-methanone | 218–220 |
| 65 | (3-amino-1H—pyrazol-4-yl)-3-furanyl-methanone | 3-dimethylamino-1-(3-pyridinyl)-2-propen-1-one | 3-furanyl[7-(3-pyridinyl)-pyrazolo[1,5-a]pyrimidin-3-yl]methanone | 236–238 |
| 66 | (3-amino-1H—pyrazol-4-yl)(3,4,5-trimethoxyphenyl)methanone | 3-dimethylamino-1-(3-pyridinyl)-2-propen-1-one | [7-(3-pyridinyl)pyrazolo-[1,5-a]pyrimidin-3-yl](3,4,5-trimethoxyphenyl)methanone | 236–237 |
| 67 | (3-amino-1H—pyrazol-4-yl)(3,4,5-trimethoxyphenyl)methanone | 3-dimethylamino-1-[3-(trifluoromethyl)phenyl]-2-propen-1-one | [7-[3-(trifluoromethyl)phenyl]pyrazolo[1,5-a]pyrimidin-3-yl](3,4,5-trimethoxyphenyl)methanone | 203–204 |
| 68 | (3-amino-1H—pyrazol-4-yl)(3,4-dimethoxyphenyl)methanone | 3-dimethylamino-1-(3-pyridinyl)-2-propen-1-one | (3,4-dimethoxyphenyl)[7-(3-pyridinyl)pyrazolo[1,5-a]-pyrimidin-3-yl]methanone | 210–211 |
| 69 | (3-amino-1H—pyrazol-4-yl)(3,4-dimethoxyphenyl)methanone | 3-dimethylamino-1-[3-(trifluoromethyl)-phenyl]-2-propen-1-one | (3,4-dimethoxyphenyl)[7-(3-(trifluoromethyl)phenyl]pyrazolo[1,5-a]pyrimidin-3-yl]methanone | 186–187 |
| 70 | (3-amino-1H—pyrazol-4-yl)(3,4-dimethoxyphen- | 3-dimethylamino-1-(3,4,5-trimethoxyphen- | (3,4-dimethoxyphenyl)[7-(3,4,5-trimethoxyphenyl)pyra- | 215–216 |

TABLE VII-continued

| Ex. | Pyrazole | 3-Dimethylamino-1-(aryl)-2-propen-1-one | Product | MP °C. |
|---|---|---|---|---|
| | yl)methanone | yl)-2-propen-1-one | zolo[1,5-a]pyrimidin-3-yl]methanone | |
| 71 | (3-amino-1H—pyrazol-4-yl)(3-methylphenyl)methanone | 3-dimethylamino-1-(3-pyridinyl)-2-propen-1-one | (3-methylphenyl)[7-(3-pyridinyl)pyrazolo[1,5-a]pyrimidin-3-yl]methanone | 156–158 |
| 72 | (3-amino-1H—pyrazol-4-yl)(3,5-dimethoxyphenyl)methanone | 3-dimethylamino-1-(3-pyridinyl)-2-propen-1-one | (3,5-dimethoxyphenyl)[7-(3-pyridinyl)pyrazolo[1,5-a]pyrimidin-3-yl]methanone | 207–208 |
| 73 | (3-amino-1H—pyrazol-4-yl)(3,4-dimethoxyphenyl)methanone | 3-dimethylamino-1-(4-pyridinyl)-2-propen-1-one | (3,4-dimethoxyphenyl)[7-(4-pyridinyl)pyrazolo[1,5-a]pyrimidin-3-yl]methanone | 232–234 |
| 74 | (3-amino-1H—pyrazol-4-yl)(3-methylphenyl)methanone | 3-dimethylamino-1-(4-pyridinyl)-2-propen-1-one | (3-methylphenyl)[7-(4-pyridinyl)pyrazolo[1,5-a]pyrimidin-3-yl]methanone | 163–165 |
| 75 | (3-amino-1H—pyrazol-4-yl)(3-methylphenyl)methanone | 3-dimethylamino-1-[3-(trifluoromethyl)phenyl]-2-propen-1-one | (3-methylphenyl)[7-[3-(trifluoromethyl)phenyl]pyrazolo[1,5-a]pyrimidin-3-yl]methanone | 163–164 |
| 76 | (3-amino-1H—pyrazol-4-yl)(3-methylphenyl)methanone | 3-dimethylamino-1-(3-methylphenyl)-2-propen-1-one | (3-methylphenyl)[7-(3-methylphenyl)pyrazolo[1,5-a]pyrimidin-3-yl]methanone | 111–113 |
| 77 | (3-amino-1H—pyrazol-4-yl)(4-chlorophenyl)methanone | 3-dimethylamino-1-[3-(trifluoromethyl)phenyl]-2-propen-1-one | (4-chlorophenyl)[7-[3-(trifluoromethyl)phenyl]pyrazolo[1,5-a]pyrimidin-3-yl)methanone | 183–185 |
| 78 | (3-amino-1H—pyrazol-4-yl)phenyl-methanone | 3-dimethylamino-1-phenyl-2-buten-1-one | (5-methyl-7-phenylpyrazolo[1,5-a]pyrimidin-3-yl)phenyl-methanone | 165–166 |
| 79 | (3-amino-1H—pyrazol-4-yl)(4-chlorophenyl)methanone | 3-dimethylamino-1-(4-pyridinyl)-2-propen-1-one | (4-chlorophenyl)[7-(4-pyridinyl)pyrazolo[1,5-a]pyrimidin-3-yl]methanone | 250–252 |
| 80 | (3-amino-1H—pyrazol-4-yl)(4-chlorophenyl)methanone | 3-dimethylamino-1-(3-pyridinyl)-2-propen-1-one | (4-chlorophenyl)[7-(3-pyridinyl)pyrazolo[1,5-a]pyrimidin-3-yl]methanone | 255–256 |
| 81 | (3-amino-1H—pyrazol-4-yl)(4-chlorophenyl)methanone | 1-[3-(trifluoromethyl)phenyl]-3-dimethylamino-2-buten-1-one | (4-chlorophenyl)[5-methyl-7-[3-(trifluoromethyl)phenyl]pyrazolo[1,5-a]pyrimidin-3-yl]methanone | 218–220 |
| 82 | (3-amino-1H—pyrazol-4-yl)(4-chlorophenyl)methanone | 3-dimethylamino-1-(4-fluorophenyl)-2-propen-1-one | (4-chlorophenyl)[7-(4-fluorophenyl)pyrazolo[1,5-a]pyrimidin-3-yl]methanone | 258–260 |
| 83 | (3-amino-1H—pyrazol-4-yl)(3-fluorophenyl)methanone | 3-dimethylamino-1-[3-(trifluoromethyl)phenyl]-2-propen-1-one | (3-fluorophenyl)[7-[3-(trifluoromethyl)phenyl]pyrazolo[1,5-a]pyrimidin-3-yl]methanone | 164–165 |
| 84 | (3-amino-1H—pyrazol-4-yl)(3-fluorophenyl)methanone | 3-dimethylamino-1-(4-fluorophenyl)-2-propen-1-one | (3-fluorophenyl)[7-(4-fluorophenyl)pyrazolo[1,5-a]pyrimidin-3-yl]methanone | 202–203 |
| 85 | (3-amino-1H—pyrazol-4-yl)-2-pyridinyl-methanone | 3-dimethylamino-1-(4-fluorophenyl)-2-propen-1-one | [7-(4-fluorophenyl)pyrazolo[1,5-a]pyrimidin-3-yl]-2-pyridinyl-methanone | 213–214 |
| 86 | (3-amino-1H—pyrazol-4-yl)(4-fluorophenyl-methanone | 3-dimethylamino-1-(4-fluorophenyl)-2-propen-1-one | (4-fluorophenyl)[7-(4-fluorophenyl)pyrazolo[1,5-a]pyrimidin-3-yl]methanone | 224–225 |
| 87 | (3-amino-1H—pyrazol-4-yl)(4-methoxyphenyl)methanone | 3-dimethylamino-1-(3-pyridinyl)-2-propen-1-one | (4-methoxyphenyl)[7-(3-pyridinyl)pyrazolo[1,5-a]pyrimidin-3-yl]methanone | 193–195 |
| 88 | (3-amino-1H—pyrazol-4-yl)(4-fluorophenyl)methanone | 3-dimethylamino-1-(4-pyridinyl)-2-buten-1-one | (4-fluorophenyl)[5-methyl-7-(4-pyridinyl)pyrazolo[1,5-a]pyrimidin-3-yl]methanone | 256–258 |
| 89 | (3-amino-1H—pyrazol-4-yl)[3-(trifluoromethyl)phenyl]methanone | 3-dimethylamino-1-(4-fluorophenyl)-2-propen-1-one | [7-(4-fluorophenyl)pyrazolo[1,5-a]pyrimidin-3-yl][3-(trifluoromethyl)phenyl]methanone | 193–194 |
| 90 | (3-amino-1H—pyrazol-4-yl)(4-methoxyphenyl)methanone | 3-dimethylamino-1-(4-pyridinyl)-2-propen-1-one | (4-methoxyphenyl)[7-(4-pyridinyl)pyrazolo[1,5-a]pyrimidin-3-yl]methanone | 235–236 |
| 91 | (3-amino-1H—pyrazol-4-yl)(3-methoxyphenyl)methanone | 3-dimethylamino-1-(4-pyridinyl)-2-propen-1-one | (3-methoxyphenyl)[7-(4-pyridinyl)pyrazolo[1,5-a]pyrimidin-3-yl]methanone | 144–146 |
| 92 | (3-amino-1H—pyrazol-4-yl)(3-methoxyphenyl)methanone | 3-dimethylamino-1-(3-pyridinyl)-2-propen-1-one | (3-methoxyphenyl)[7-(3-pyridinyl)pyrazolo[1,5-a]pyrimidin-3-yl]methanone | 166–168 |
| 93 | (3-amino-1H—pyrazol-4-yl)[4-(trifluoromethyl)phenyl]methanone | 3-dimethylamino-1-[4-(trifluoromethyl)phenyl]-2-propen-1-one | [4-(trifluoromethyl)phenyl][7-[4-(trifluoromethyl)phenyl]pyrazolo[1,5-a]pyrimidin-3-yl]methanone | Syrup |
| 94 | (3-amino-1H—pyrazol-4-yl)(3-chlorophenyl)methanone | 3-dimethylamino-1-(4-pyridinyl)-2-propen-1-one | (3-chlorophenyl)[7-(4-pyridinyl)pyrazolo[1,5-a]pyrimidin-3-yl]methanone | 196–198 |
| 95 | (3-amino-1H—pyrazol-4- | 3-dimethylamino-1-(3- | (3-chlorophenyl)[7-(3-pyridin- | Syrup |

TABLE VII-continued

| Ex. | Pyrazole | 3-Dimethylamino-1-(aryl)-2-propen-1-one | Product | MP °C. |
|---|---|---|---|---|
| | yl)(3-chlorophenyl)methanone | pyridinyl)-2-propen-1-one | yl)pyrazolo[1,5-a]pyrimidin-3-yl]methanone | |
| 96 | (3-amino-1H—pyrazol-4-yl)[4-(trifluoromethyl)phenyl]methanone | 3-dimethylamino-1-(3,4-dichlorophenyl)-2-propen-1-one | [7-(3,4-dichlorophenyl)pyrazolo[1,5-a]pyrimidin-3-yl][4-(trifluoromethyl)phenyl]methanone | 170–172 |
| 97 | (3-amino-1H—pyrazol-4-yl)(4-fluorophenyl)methanone | 3-dimethylamino-2-methyl-1-(3-pyridinyl)-2-propen-1-one | (4-fluorophenyl)[6-methyl-7-(3-pyridinyl)pyrazolo[1,5-a]pyrimidin-3-yl]methanone | 182–183 |
| 98 | (3-amino-1H—pyrazol-4-yl)(3-chlorophenyl)methanone | 3-dimethylamino-1-(4-fluorophenyl)-2-propen-1-one | (3-chlorophenyl)[7-(4-fluorophenyl)pyrazolo[1,5-a]pyrimidin-3-yl]methanone | 198–200 |
| 99 | (3-amino-1H—pyrazol-4-yl)(2,5-dichlorophenyl)methanone | 3-dimethylamino-1-(4-fluorophenyl)-2-propen-1-one | (2,5-dichlorophenyl)[7-(4-fluorophenyl)pyrazolo[1,5-a]pyrimidin-3-yl]methanone | 191–192 |
| 100 | (3-amino-1H—pyrazol-4-yl)(2,5-dichlorophenyl)methanone | 3-dimethylamino-1-(3-pyridinyl)-2-propen-1-one | (2,5-dichlorophenyl)[7-(3-pyridinyl)pyrazolo[1,5-a]pyrimidin-3-yl]methanone | 201–203 |
| 101 | (3-amino-1H—pyrazol-4-yl)(2,5-dichlorophenyl)methanone | 3-dimethylamino-1-(4-pyridinyl)-2-propen-1-one | (2,5-dichlorophenyl)[7-(4-pyridinyl)pyrazolo[1,5-a]pyrimidin-3-yl]methanone | 189–190 |
| 102 | (3-amino-1H—pyrazol-4-yl)phenylmethanone | 3-dimethylamino-1-[4-(methylthio)phenyl]-2-propen-1-one | [7-[4-(methylthio)phenyl]pyrazolo[1,5-a]pyrimidin-3-yl]phenylmethanone | 141–142 |
| 103 | (3-amino-1H—pyrazol-4-yl)(2-methylphenyl)methanone | 3-dimethylamino-1-(3-pyridinyl)-2-propen-1-one | (2-methylphenyl)[7-(3-pyridinyl)pyrazolo[1,5-a]pyrimidin-3-yl]methanone | 178–180 |
| 104 | (3-amino-1H—pyrazol-4-yl)(2-methylphenyl)methanone | 3-dimethylamino-1-(4-pyridinyl)-2-propen-1-one | (2-methylphenyl)[7-(4-pyridinyl)pyrazolo[1,5-a]pyrimidin-3-yl]methanone | 125–126 |
| 105 | (3-amino-1H—pyrazol-4-yl)(2-chlorophenyl)methanone | 3-dimethylamino-1-(4-pyridinyl)-2-propen-1-one | (2-chlorophenyl)[7-(4-pyridinyl)pyrazolo[1,5-a]pyrimidin-3-yl]methanone | 78–81 |
| 106 | (3-amino-1H—pyrazol-4-yl)(2-methylphenyl)methanone | 3-dimethylamino-1-[4-(trifluoromethyl)phenyl]-2-propen-1-one | (2-methylphenyl)[7-(4-trifluoromethyl)phenyl]pyrazolo[1,5-a]pyrimidin-3-yl]methanone | 187–189 |
| 107 | (3-amino-1H—pyrazol-4-yl)-4-pyridinylmethanone | 3-dimethylamino-1-(3-pyridinyl)-2-propen-1-one | 4-pyridinyl[7-(3-pyridinyl)pyrazolo[1,5-a]pyrimidin-3-yl]methanone | 253–255 |
| 108 | (3-amino-1H—pyrazol-4-yl)-4-pyridinylmethanone | 3-dimethylamino-1-[3-(trifluoromethyl)phenyl]-2-propen-1-one | 4-pyridinyl[7-[3-trifluoromethyl)phenyl]pyrazolo[1,5-a]pyrimidin-3-yl]methanone | 157–159 |
| 109 | (3-amino-1H—pyrazol-4-yl)-4-pyridinylmethanone | 3-dimethylamino-1-(4-fluorophenyl)-2-propen-1-one | [7-(4-fluorophenyl)pyrazolo[1,5-a]pyrimidin-3-yl]-4-pyridinylmethanone | 263–265 |
| 110 | (3-amino-1H—pyrazol-4-yl)-2-pyridinylmethanone | 3-dimethylamino-1-[4-(trifluoromethyl)phenyl]-2-propen-1-one | 2-pyridinyl[7-[4-(trifluoromethyl)phenyl]pyrazolo[1,5-a]pyrimidin-3-yl]methanone | 217–218 |
| 111 | (3-amino-1H—pyrazol-4-yl)[4-(dimethylamino)phenyl]methanone | 3-dimethylamino-1-(3-pyridinyl)-2-propen-1-one | [4-(dimethylamino)phenyl][7-(3-pyridinyl)pyrazolo[1,5-a]pyrimidin-3-yl]methanone | 226–228 |
| 112 | (3-amino-1H—pyrazol-4-yl)[4-(dimethylamino)phenyl]methanone | 3-dimethylamino-1-(4-pyridinyl)-2-propen-1-one | [4-(dimethylamino)phenyl][7-(4-pyridinyl)pyrazolo[1,5-a]pyrimidin-3-yl]methanone | 224–225 |
| 113 | (3-amino-1H—pyrazol-4-yl)[4-(dimethylamino)phenyl]methanone | 3-dimethylamino-1-[3-(trifluoromethyl)phenyl]-2-propen-1-one | [4-(dimethylamino)phenyl][7-[3-(trifluoromethyl)phenyl]pyrazolo[1,5-a]pyrimidin-3-yl]methanone | 153–155 |
| 114 | (3-amino-5-methyl-1H—pyrazol-4-yl)phenylmethanone | 3-dimethylamino-1-(4-pyridinyl)-2-propen-1-one | [2-methyl-7-(4-pyridinyl)pyrazolo[1,5-a]pyrimidin-3-yl]phenylmethanone | 178–180 |
| 115 | (3-amino-1H—pyrazol-4-yl)phenylmethanone | 3-dimethylamino-2-methyl-1-[3-(trifluoromethyl)phenyl]-2-propen-1-one | [6-methyl-7-[3-(trifluoromethyl)phenyl]pyrazolo[1,5-a]pyrimidin-3-yl]methanone | 174–175 |
| 116 | (3-amino-1H—pyrazol-4-yl)(2-methoxyphenyl)methanone | 3-dimethylamino-1-(3-pyridinyl)-2-propen-1-one | (2-methoxyphenyl)[7-(3-pyridinyl)pyrazolo[1,5-a]pyrimidin-3-yl]methanone | 144–145 |
| 117 | (3-amino-1H—pyrazol-4-yl)[3,4-(methylenedioxy)phenyl]methanone | 3-dimethylamino-1-(3-pyridinyl)-2-propen-1-one | 1,3-benzodioxol-5-yl[7-(3-pyridinyl)pyrazolo[1,5-a]pyrimidin-3-yl]methanone | 212–213 |
| 118 | (3-amino-1H—pyrazol-4-yl)[3,4-methylenedioxy)phenyl]methanone | 3-dimethylamino-1-(4-pyridinyl)-2-propen-1-one | 1,3-benzodioxol-5-yl[7-(4-pyridinyl)pyrazolo[1,5-a]pyrimidin-3-yl]methanone | 236–237 |
| 119 | (3-amino-1H—pyrazol-4-yl)(4-ethoxyphenyl)methanone | 3-dimethylamino-1-(3-pyridinyl)-2-propen-1-one | (4-ethoxyphenyl)[7-(3-pyridinyl)pyrazolo[1,5-a]pyrimidin-3-yl]methanone | 193–194 |
| 120 | (3-amino-1H—pyrazol-4-yl)-2-naphthalenylmethanone | 3-dimethylamino-1-(3-pyridinyl)-2-propen-1-one | 2-naphthalenyl[7-(3-pyridinyl)pyrazolo[1,5-a]pyrimidin-3-yl]methanone | 218–220 |

TABLE VII-continued

| Ex. | Pyrazole | 3-Dimethylamino-1-(aryl)-2-propen-1-one | Product | MP °C. |
|---|---|---|---|---|
| 121 | (3-amino-1H—pyrazol-4-yl)-2-thienylmethanone | 3-dimethylamino-1-[4-(trifluoromethyl)-phenyl]-2-propen-1-one | 2-thienyl[7-[4-(trifluoromethyl)phenyl]pyrazolo[1,5-a]-pyrimidin-3-yl]methanone | 191–193 |
| 122 | (3-amino-1H—pyrazol-4-yl)-2-thienylmethanone | 3-dimethylamino-1-(3-fluorophenyl)-2-propen-1-one | [7-(3-fluorophenyl)pyrazolo-[1,5-a]pyrimidin-3-yl]-2-thienylmethanone | 235–237 |
| 123 | (3-amino-1H—pyrazol-4-yl)(2-methoxyphenyl)-methanone | 3-dimethylamino-1-(4-fluorophenyl)-2-propen-1-one | [7-(4-fluorophenyl)pyrazolo-[1,5-a]pyrimidin-3-yl](2-methoxyphenyl)methanone | 193–194 |
| 124 | (3-amino-1H—pyrazol-4-yl)(5-methyl-2-thienyl)methanone | 3-dimethylamino-1-(3-pyridinyl)-2-propen-1-one | (5-methyl-2-thienyl)[7-(3-pyridinyl)pyrazolo[1,5-a]pyrimidin-3-yl]methanone | 185–187 |
| 125 | (3-amino-1H—pyrazol-4-yl)-3-thienylmethanone | 3-dimethylamino-1-[3-(trifluoromethyl)-phenyl]-2-propen-1-one | 3-thienyl[7-[3-(trifluoromethyl)phenyl]pyrazolo[1,5-a]pyrimidin-3-yl]methanone | 124–125 |
| 126 | (3-amino-1H—pyrazol-4-yl)-3-thienylmethanone | 3-dimethylamino-1-(3-pyridinyl)-2-propen-1-one | [7-(3-pyridinyl)pyrazolo-[1,5-a]pyrimidin-3-yl]-3-thienylmethanone | 203–204 |
| 127 | (3-amino-1H—pyrazol-4-yl)(4-ethylphenyl)-methanone | 3-dimethylamino-1-(3-pyridinyl)-2-propen-1-one | (4-ethylphenyl)[7-(3-pyridinyl)pyrazolo[1,5-a]pyrimidin-3-yl]methanone | 143–144 |
| 128 | (3-amino-1H—pyrazol-4-yl)-3-thienylmethanone | 3-dimethylamino-1-(4-pyridinyl)-2-propen-1-one | [7-(4-pyridinyl)pyrazolo-[1,5-a]pyrimidin-3-yl]-3-thienylmethanone | 197–198 |
| 129 | (3-amino-1H—pyrazol-4-yl)(2-fluorophenyl)-methanone | 3-dimethylamino-1-(4-pyridinyl)-2-propen-1-one | (2-fluorophenyl)[7-(4-pyridinyl)pyrazolo[1,5-a]pyrimidin-3-yl]methanone | 188–189 |
| 130 | (3-amino-1H—pyrazol-4-yl)(2-fluorophenyl)-methanone | 3-dimethylamino-1-(3-pyridinyl)-2-propen-1-one | (2-fluorophenyl)[7-(3-pyridinyl)pyrazolo[1,5-a]pyrimidin-3-yl]methanone | 164–165 |
| 131 | (3-amino-1H—pyrazol-4-yl)(2-fluorophenyl)-methanone | 3-dimethylamino-1-[3-(trifluoromethyl)-phenyl]-2-propen-1-one | (2-fluorophenyl)[7-[3-(trifluoromethyl)phenyl]pyrazolo[1,5-a]pyrimidin-3-yl]methanone | 155–157 |

EXAMPLE 132

Phenyl[7-(4-pyridinyl)pyrazolo[1,5-a]pyrimidin-3-yl]methanone, pyridine-1-oxide

A 3.0 g portion of [7-(4-pyridinyl)pyrazolo[1,5-a]pyrimidin-3-yl]methanone was dissolved in 200 ml of methylene chloride. A 2.0 g portion of 80–90% m-chloroperbenzoic acid was added and the mixture was stirred for 18 hours. The solid was collected, air dried, slurried in 50 ml of saturated aqueous sodium bicarbonate, added to 150 ml of water and heated to boiling. The solution was clarified while hot, then cooled. The solid was washed with water and air dried at 50° C., giving 0.4 g of the desired product, mp 239°–244° C.

EXAMPLE 133

(4-Fluorophenyl)[7-(4-pyridinyl)pyrazolo[1,5-a]pyrimidin-3-yl]methanone, pyridine-1-oxide A 1.6 g portion of (4-fluorophenyl)[7-(4-pyridinyl)-pyrazolo[1,5-a) pyrimidin-3-yl]methanone was reacted as described in Example 132, giving 1.0 g of the desired product, mp 283°–285° C. (dec.).

EXAMPLE 134

[5-Methyl-7-(4-pyridinyl)pyrazolo[1,5-a]pyrimidin-3-yl]phenyl-methanone, pyridine-1-oxide A 2.1 g portion of [5-methyl-7-(4-pyridinyl)-pyrazolo[1,5-a]pyrimidin-3-yl]phenyl-methanone was reacted as described in Example 132, giving 1.8 g of the desired product, mp 249°–250° C.

EXAMPLE 135

Phenyl(7-phenylpyrazolo[1,5-a]pyrimidin-3-yl)methanone

A mixture of 0.01 mole of 3-chloro-3-phenyl-2-propenal and 0.01 mole of (3-amino-1H-pyrazol-4-yl)phenylmethanone in 25 ml of acetic acid was refluxed for 6 hours. The solvent was removed in vacuo and the product isolated as described in Example 1, giving the desired product as crystals, mp 163°–165° C.

EXAMPLE 136

2-Furanyl[7-(3-pyridinyl)pyrazolo[1,5-a]pyrimidin-3-yl]methanone

A mixture of 0.02 mole of 3-chloro-3-(3-pyridinyl)-2-propenal and 0.02 mole of (3-amino-1H-pyrazol-4-yl)-2-furanyl-methanone in 30 ml of glacial acetic acid was refluxed for 5 hours. The solvent was removed in vacuo and the residue partitioned between saturated aqueous sodium bicarbonate and dichloromethane. The dichloromethane layer was dried over sodium sulfate and passed through a short pad of hydrous magnesium silicate. The eluent was concentrated and the residue crystallized from dichloromethane:hexane to give the desired product as crystals, mp 228°–229° C.

EXAMPLE 137

2-Furanyl[7-(3-pyridinyl)pyrazolo[1,5-a]pyrimidin-3-yl]methanone

A mixture of 0.1 mole of 3-dimethylamino-1-(3-pyridinyl)-2-propen-1-one and a 0.15 mole of pyrrolidine in 200 ml of xylene was refluxed with distillation of the xylene by passing a stream of argon through the solution. Additional xylene was added periodically. After 10 hours the solvent was removed to give crude 3-(1-pyrrolidinyl)-1-(3-pyridinyl)-2-propen-1-one. This crude compound and 0.1 mole of (3-amino-1H-pyrazol-4-yl)-2-furanyl-methanone in 100 ml of glacial acetic acid was refluxed for 8 hours. The solvent was removed in vacuo and the product isolated as described in Example 1, giving the desired product as crystals, mp 228°–229° C.

EXAMPLE 138

[5-Methyl-7-[3-(trifluoromethyl)phenyl]pyrazolo[1,5-a]pyrimidin-3-yl]phenyl-methanone A mixture of 0.05 mole of 1-[3-[3-(trifluoromethyl)phenyl]butan-1,3-dione and 0.05 mole of (3-amino-1H-pyrazol-4-yl)phenyl-methanone in 40 ml of glacial acetic acid was refluxed for 10 hours. The solvent was removed in vacuo and the residue partitioned between saturated aqueous sodium bicarbonate and dichloromethane. The dichloromethane layer was dried over sodium sulfate and passed through a short pad of hydrous magnesium silicate. The eluent was concentrated and the residue was crystallized from dichloromethane:hexane to give the desired product as crystals, mp 153°–154° C.

EXAMPLE 139

(5-Methyl-7-phenylpyrazolo[1,5-a]pyrimidin-3-yl)phenyl-methanone

A mixture of 0.01 mole of 1-(3-phenyl)butan-1,3-dione and 0.01 mole of (3-amino-1H-pyrazol-4-yl)phenyl-methanone in 25 ml of n-butanol was refluxed for 8 hours. The solvent was removed and the product isolated as described in Example 1, giving the desired product as crystals, mp 165°–166° C.

EXAMPLE 140

[5-Methyl-7-(4-pyridinyl)pyrazolo[1,5-a]pyrimidin-3-yl]phenyl-methanone

A mixture of 0.05 mole of 3-(1-pyrrolidinyl)-1-(4-pyridinyl)-2-buten-1-one and 0.05 ml of (3-amino-1H-pyrazol-4-yl)phenyl-methanone in 50 ml of glacial acetic acid was refluxed for 8 hours. The solvent was removed and the residue partitioned between saturated aqueous sodium bicarbonate and dichloromethane. The dichloromethane layer was washed with water, dried over magnesium sulfate and passed through a short pad of hydrous magnesium silicate. The eluent was concentrated and the residue crystallized from dichloromethane:hexane, giving the desired product, mp 209°–210° C.

EXAMPLE 141

Phenyl[7-[(3-trifluoromethyl)phenyl]pyrazolo[1,5-a]pyrimidin-3-yl]methanone

A mixture of 100 ml of diethyl ether, 3.36 g of sodium hydride (60% in oil), 7.4 g of ethyl formate and 18.8 g of m-trifluoromethylacetophenone was refluxed with vigorous stirring for 2 hours, then cooled and the precipitate collected, giving 14.6 g of the sodium salt of 3-hydroxy-3-(trifluoromethyl)acrylophenone.

A suspension of 12.0 g of the above compound in 75 ml of dioxane and 10 ml of acetic anhydride was stirred at room temperature for 2 hours and then poured into water. The precipitate was collected, dissolved in dichloromethane and passed through a short pad of hydrous magnesium silicate. The eluent was concentrated and hexane added, giving 3-hydroxy-3'-(trifluoromethyl)acrylophenone acetate as crystals, mp 55°–57° C. A mixture of 0.03 mole of these crystals and 0.03 mole of (3-amino-1H-pyrazol-4-yl)phenyl-methanone in 30 ml of glacial acetic acid was refluxed for 5 hours. The solvent was removed and the residue partitioned between saturated aqueous sodium bicarbonate and dichloromethane. The dichloromethane layer was dried over magnesium sulfate and passed through a short pad of hydrous magnesium silicate. The eluent was concentrated and diluted with hexane, giving the desired product as crystals, mp 148°–150° C.

EXAMPLE 142

Phenyl[7-(3-pyridinyl)pyrazolo[1,5-a]pyrimidin-3-yl]methanone

A mixture of 0.02 mole of 3-chloro-3-(3-pyridinyl)-2-propenal and 0.02 mole of (3-amino-1H-pyrazol-4-yl)phenyl-methanone in 25 ml of glacial acetic acid was refluxed for 5 hours. The solvent was removed and the product isolated as described in Example 1, giving the desired product as crystals, mp 202°–203° C.

EXAMPLE 143

Phenyl(7-phenylpyrazolo[1,5-a]pyrimidin-3-yl)methanone

A mixture of 3.2 g (0.02 mole) of 3-chloro-3-phenyl-2-propenal and 0.02 mole of (3-amino-1H-pyrazol-4-yl)phenyl-methanone in 25 ml of glacial acetic acid was refluxed for 6 hours. The solvent was removed and the product was isolated as described in Example 1, giving crystals, mp 163°–165° C.

EXAMPLE 144

[5-Methyl-7-(3-pyridinyl)pyrazolo[1,5-a]pyrimidin-3-yl]phenyl-methanone

A mixture of 8.16 g (0.05 mole) of 1-(3-pyridinyl)butan-1,3-dione and 0.05 mole of (3-amino-1H-pyrazol-4-yl)phenyl-methanone in 40 ml of glacial acetic acid was refluxed for 8 hours. The solvent was removed in vacuo and the product isolated as described in Example 1, giving the desired product as crystals, mp 196°–198° C.

EXAMPLE 145

[5-Methyl-7-(3-pyridinyl)pyrazolo[1,5-a]pyrimidin-3-yl]phenyl-methanone

A mixture of 8.16 g (0.05 mole) of 1-(3-pyridinyl)butan-1,3-dione and 0.05 mole of (3-amino-1H-pyrazol-4-yl)phenyl-methanone in xylene was refluxed for 20 hours. The solvent was removed and the residue dissolved in dichloromethane. This solution was filtered, dried over magnesium sulfate and passed through a short pad of hydrous magnesium silicate. The eluent was concentrated with hexane added during concentration. Cooling and filtration gave the desired product as crystals, mp 196°–198° C.

EXAMPLE 146

[5-Methyl-7-(3-pyridinyl)pyrazolo[1,5-a]pyrimidin-3-yl]phenyl-methanone

To a solution of 16.32 g of 1-(3-pyridinyl)butan-1,3-dione in 200 ml of ethyl acetate was added 7.11 g of pyrrolidone. The mixture was stirred at room temperature and then the crystals were collected giving 7.0 g of 3-(1-pyrrolidinyl)-1-(3-pyridinyl)-2-buten-1-one, mp 116°–118° C.

A 0.02 mole portion of the above compound and 0.02 mole of (3-amino-1H-pyrazol-4-yl)phenyl-methanone in 25 ml of glacial acetic acid was refluxed for 8 hours. The solvent was removed and the product isolated as described in Example 1, giving the desired product as crystals, mp 196°–198° C.

EXAMPLE 147

Phenyl[7-[(3-trifluoromethyl)phenyl]pyrazolo[1,5-a]pyrimidin-3-yl]methanone

A mixture of 0.10 mole of 3-dimethylamino-1-[(3-trifluoromethyl)phenyl]-2-propen-1-one and 0.10 mole of p-toluenesulfonic acid in 100 ml of ethanol was warmed at 60° C. for 12 hours and the solvent removed in vacuo. The residue was partitioned between dichloromethane and water. The organic layer was dried over magnesium sulfate and concentrated, giving crude 3-ethoxy-1-[(3-trifluoromethyl)phenyl]-2-propen-1-one.

A mixture of the above compound and 0.10 mole of (3-amino-1H-pyrazol-4-yl)phenyl-methanone in 75 ml of glacial acetic acid was refluxed for 5 hours. The solvent was removed and the product isolated as described in Example 1, giving the desired product as crystals, mp 148°–150° C.

EXAMPLE 148

Phenyl[7-(3-pyridinyl)pyrazolo[1,5-a]pyrimidin-3-yl]methanone

A mixture of 0.02 mole of 3-ethoxy-1-(3-pyridinyl)-2-propen-1-one, 0.02 mole of (3-amino-1H-pyrazol-4-yl)phenyl-methanone and 100 ml of xylene was refluxed for 12 hours. The solvent was removed and the residue dissolved in dichloromethane. This solution was dried over sodium sulfate and the product isolated as described in Example 1, as crystals, mp 202°–203° C.

EXAMPLE 149

2-Pyridinyl[7-(3-pyridinyl)pyrazolo[1,5-a]pyrimidin-3-yl]methanone

A mixture of 0.10 mole of 3-dimethylamino-1-(3-pyridinyl)-2-propen-1-one and 0.20 mole of p-toluenesulfonic acid in 150 ml of anhydrous ethanol was refluxed for 10 hours. The solvent was removed and the residue partitioned between water and dichloromethane. The organic layer was dried over magnesium sulfate and the solvent removed, giving 3-ethoxy-1-(3-pyridinyl)-2-propen-1-one.

The above compound was reacted with (3-amino-1H-pyrazol-4-yl)-2-pyridinyl-methanone in acetic acid as described in Example 1, giving the desired product as crystals, mp 216°–218° C.

EXAMPLE 150

(4-Methylphenyl)[7-(3-pyridinyl)pyrazolo[1,5-a]pyrimidin-3-yl]methanone

A mixture of 0.10 mole of 3-acetylpyridine and 0.10 mole of N,N-dimethylformamide dimethylacetal in 100 ml of benzene was refluxed for 12 hours. The solvent was removed, giving 3-dibutylamino-1-(3-pyridinyl)-2-propen-1-one.

The above compound was reacted with (3-amino-1H-pyrazol-4-yl) (4-methylphenyl)methanone in glacial acetic acid as described in Example 1, giving the desired product as crystals, mp 203°–204° C.

EXAMPLE 151

(4-Methoxyphenyl)[7-(3-pyridinyl)pyrazolo[1,5-a]pyrimidin-3-yl]methanone

A mixture of 0.10 mole of 3-acetylpyridine and 0.10 mole of N,N-diethylformamide dimethylacetal in 100 ml of dioxane was refluxed for 10 hours. The solvent was removed, giving 3-diethylamino-1-(3-pyridinyl)-2-propen-1-one.

A mixture of 0.10 mole of the above compound and 0.10 mole of (3-amino-1H-pyrazol-4-yl) (4-methoxyphenyl)methanone in glacial acetic acid was refluxed for 6 hours. The product was isolated as described in Example 1, giving crystals, mp 193°–195° C.

EXAMPLE 152

2-pyridinyl[7-[3-(trifluoromethyl)phenyl]pyrazolo[1,5-a]pyrimidin-3-yl]methanone A mixture of 0.10 mole of 3-acetylpyridine and 0.10 mole of N,N-dimethylformamide dicyclohexylacetal in 100 ml of dioxane was refluxed for 8 hours. The solvent was removed in vacuo, giving 3-dimethylamino-1-[3-(trifluoromethyl)phenyl]-2-propen-1-one. The above compound was reacted with (3-amino-1H-pyrazol-4-yl)-2-pyridinyl-methanone as described in Example 1, giving the desired product as crystals, mp 166°–167° C.

EXAMPLE 153

2-Pyridinyl[7-(3-pyridinyl)pyrazolo[1,5-a]pyrimidinyl-3-yl]methanone

A mixture of 25 g of 3-acetylpyridine and 35 ml of N,N-dimethylformamide dipropylacetal was heated at 100° C. for 6 hours. The mixture was concentrated in vacuo and the residue crystallized, giving 3-dimethylamino-1-(3-pyridinyl)-2-propen-1-one.

The above compound was reacted with (3-amino-1H-pyrazol-4-yl)-2-pyridinyl-methanone as described in Example 1, giving the desired product as crystals, mp 216°–218° C.

EXAMPLE 154

(4-Methylphenyl)[7-(3-pyridinyl)pyrazolo[1,5-a]pyrimidin-3-yl]methanone

To a mixture of 0.10 mole of 3-acetylpyridine in 100 ml of tetrahydrofuran was added 0.10 mole of tert.-butoxy-bis-(dimethylamino)methane. The mixture was stirred for 24 hours and the solvent removed, giving 3-dimethylamino-1-(3-pyridinyl)-2-propen-1-one.

The above compound was reacted with (3-amino-1H-pyrazol-4-yl) (4-methylphenyl)methanone as described in Example 1, giving the desired product as crystals, mp 203°–204° C.

EXAMPLE 155

2-Furanyl[7-(3-pyridinyl)pyrazolo[1,5-a]pyrimidin-3-yl]methanone

A mixture of 0.02 mole of 3-acetylpyridine and 0.022 mole of tris(dimethylamino)methane in benzene was refluxed for 5 hours, giving 3-dimethylamino-1-(3-pyridinyl)-2-propen-1-one.

The above compound was reacted with (3-amino-1H-pyrazol-4-yl)-2-furanyl-methanone as described in Example 1, giving the desired product as crystals, mp 228°–229° C.

EXAMPLE 156

Phenyl-[7-(4-pyridinyl)pyrazolo[1,5-a]pyrimidin-3-yl]methanone

A mixture of 0.10 mole of 4-acetylpyridine and 40 ml of N,N-dimethylformamide diethylacetal was refluxed for 5 hours. The mixture was concentrated in vacuo, giving 3-dmethylamino-1-(4-pyridinyl)-2-propen-1-one.

The above compound (0.05 mole) and 0.05 mole of (3-amino-1H-pyrazol-4-yl)phenyl-methanone were reacted as described in Example 1, giving the desired product as crystals, mp 185°–186° C.

EXAMPLE 157

Phenyl[7-[(3-trifluoromethyl)phenyl]pyrazolo[1,5-a]pyrimidin-3-yl]methanone

A mixture of 0.10 mole of m-trifluoromethylacetophenone and 100 ml of N,N-dimethylformamide dibutylacetal was heated to 100° C. for 10 hours. The mixture was concentrated in vacuo and the residue crystallized, giving 3-dimethylamino-1-[(3-trifluoromethyl)phenyl]-2-propen-1-one.

A 0.05 mole portion of the above compound was reacted with 0.05 mole of (3-amino-1H-pyrazol-4-yl)phenylmethanone as described in Example 1, giving the desired product as crystals, mp 148°–150° C.

EXAMPLE 158

(4-Fluorophenyl)[7-(4-pyridinyl)pyrazolo[1,5-a]pyrimidin-3-yl]methanone

A mixture of 0.10 mole of 4-acetylpyridine and 0.12 mole of N,N-dimethylformamide dibenzylacetal in benzene was refluxed for 8 hours, giving 3-dimethylamino-1-(4-pyridinyl)-2-propen-1-one.

A 0.05 mole portion of the above compound and 0.05 mole of (3-amino-1H-pyrazol-4-yl)(4-fluorophenyl)methanone were reacted as described in Example 1, giving the desired product as crystals, mp 214°–216° C.

EXAMPLE 159

[7-(3-Pyridinyl)pyrazolo[1,5-a]pyrimidin-3-yl]-2-thiazolyl-methanone

As described for Example 1, (3-amino-1H-pyrazol-4-yl)-2-thiazolyl-methanone was reacted with 3-dimethylamino-1-(3-pyridinyl)-2-propen-1-one to give the product as colorless crystals, mp 262°–264° C.

EXAMPLE 160

[7-(4-Pyridinyl)pyrazolo[1,5-a]pyrimidin-3-yl]-2-thiazolyl-methanone

As described for Example 1, (3-amino-1H-pyrazol-4-yl)-2-thiazolyl-methanone was reacted with 3-dimethylamino-1-(4-pyridinyl)-2-propen-1-one to give the product as crystals, mp 323°–325° C.

EXAMPLE 161

2-Furanyl(7-phenylpyrazolo[1,5-a]pyrimidin-3-yl)methanone

A mixture of 0.86 g of (3-amino-1H-pyrazol-4-yl)-2-furanylmethanone and 0.63 g of 1-phenyl-1-propynone in 35 ml of ethanol was heated on a steam bath for one hour, then chilled in an ice bath. The solid was collected giving 0.43 g of intermediate uncyclized product, mp 190°–194° C.

A 100 mg portion of this intermediate was heated in 20 ml of ethanol containing a catalytic amount of p-toluenesulfonic acid for 20 minutes on a steam bath. The solvent was removed and the residue partitioned between dichloromethane and dilute sodium hydroxide. The organic layer was heated and concentrated while adding hexane. When crystals began to form, the mixture was allowed to cool to room temperature. Filtration gave 75 mg of the desired product as off-white crystals having a melting point of 185°–187° C. and a pmr spectrum identical to that of the product prepared as described in Example 22.

EXAMPLE 162

2-Furanyl(7-phenylpyrazolo[1,5-a]pyrimidin-3-yl)methanone

A mixture of 0.86 g of (3-amino-1H-pyrazol-4-yl)-2-furanylmethanone and 0.63 g of 1-phenyl-1-propynone in 25 ml of ethanol with a catalytic amount of p-toluenesulfonic acid was heated on a steam bath for 1.5 hours. The mixture was chilled and then filtered giving 1.0 g of yellow solid. This solid was dissolved in a small amount of dichloromethane and placed on a silica gel column. The column was eluted with ethyl acetate:hexane (1:20) with a gradual change to ethyl acetate:hexane (2:5) as eluent. The column was then washed with ethyl acetate and the ethyl acetate wash was concentrated to a solid. This solid was cyrstallized from dichloromethane, giving 0.85 g of the desired product as cream crystals having a melting point of 188°–190° C. and a pmr spectrum identical to that of the product prepared as described in Example 22.

EXAMPLE 163

2-Furanyl(7-phenylpyrazolo[1,5-a]pyrimidin-3-yl)methanone

A mixture of 0.86 g of (3-amino-1H-pyrazol-4-yl)-2-furanylmethanone and 0.63 g of 1-phenyl-1-propynone in 35 ml of ethanol with several drops of boron trifluoride etherate was refluxed for 18 hours. The solvent was removed and the residue chromatographed on silica gel with ethyl acetate:hexane (1:20) as eluent and a gradual change to ethyl acetate:hexane (2:5). Elution with ethyl acetate gave a solid which was recrystallized from dichloromethanehexane, giving the desired product, mp 185°–187° C.

EXAMPLE 164

Phenyl[7-(3-pyridinyl)pyrazolo[1,5-a]pyrimidin-3-yl]methanone, pyridine-1-oxide

A 1.5 g portion of phenyl[7-(3-pyridinyl)pyrazolo[1,5-a]pyrimidin-3-yl]methanone in 200 ml of dichloromethane was reacted as described in Example 132, giving 1.05 g of the desired product, mp 265°–267° C.

EXAMPLE 165

(4-Methoxyphenyl)[7-(3-pyridinyl)pyrazolo[1,5-a]pyrimidin-3-yl]methanone, pyridine-1-oxide A 1.65 g portion of (4-methoxyphenyl)[7-(3-pyridinyl)pyrazolo[1,5-a]pyrimidin-3-yl]methanone in 200 ml of dichloromethane was reacted as described in Example 132, giving 0.37 g of the desired product, mp 254°–257° C.

EXAMPLE 166

[7-[3-(Ethylamino)phenyl]pyrazolo[1,5-a]pyrimidin-3-yl]-2-furanylmethanone

N-(3-Acetylphenyl)-4-methylbenzenesulfonamide was prepared by the method of R. H. Vloth, et al., J. Med. Chem., 9, 88 (1966).

A 29 g portion of N-(3-acetylphenyl)-4-methylbenzenesulfonamide was dissolved in 250 ml of dimethylformamide with stirring. This mixture was treated with 6.5 g of sodium methoxide and stirred for 30 minutes, then 20 g of ethyl iodide was added. This mixture was stirred at room temperature for one hour, then at reflux for 5 hours. The dimethylformamide was removed in vacuo, the residue shaken with 150 ml of water, the mixture adjusted to pH 4 with 10N sodium hydroxide and then cooled to 0° C. The precipitate was collected, washed twice with water and then air dried, giving 31.5 g of N-(3-acetylphenyl)-N-ethyl-4-methylbenzenesulfonamide.

A 31.2 g portion of N-(3-acetylphenyl)-N-ethyl-4-methylbenzenesulfonamide and 50 ml of dimethylformamide dimethylacetal were combined and stirred on a steam bath for 18 hours, then evaporated in vacuo to an oil. This oil was triturated with hexane at −10° C. The hexane was decanted and the residue dissolved in 125 ml of boiling dichloromethane and then filtered. The filtrate was reheated to boiling, 200 ml of hexane was added and the mixture cooled to −10° C. The precipitate was collected, washed with hexane and dried, giving 21.6 g of N-[3-[3-(dimethylamino)-1-oxo-2-propenyl]phenyl]-N-ethyl-4-methylbenzenesulfonamide.

A mixture of 5.9 g of (3-amino-1H-pyrazol-4-yl)-2-furanylmethanone, 12.4 g of N-[3-[3-(dimethylamino)-1-oxo-2-propenyl]phenyl]-N-ethyl-4-methylbenzenesulfonamide and 200 ml of glacial acetic acid was refluxed for 18 hours, then cooled to room temperature and evaporated to dryness. The residue was partitioned between 200 ml of dichloromethane and 100 ml of saturated aqueous sodium bicarbonate. The dichloromethane layer was dried, then filtered through hydrous magnesium silicate and washed with 200 ml of dichloromethane. The filtrate and wash were combined with 200 ml of hexane, concentrated to 250 ml, diluted with 100 ml of hexane and concentrated to turbidity. A heavy oil formed which was separated and cooled to −10° C. producing a solid. This solid was washed with hexane and then dried in vacuo at 60° C. giving N-ethyl-N-[3-[3-(2-furanylcarbonyl)pyrazolo[1,5-a]pyrimidin-7-yl]phenyl]-4-methylbenzenesulfonamide.

A 10.7 g portion of N-ethyl-N-[3-[3-(2-furanylcarbonyl)pyrazolo[1,5-a]pyrimidin-7-yl]phenyl]-4-methylbenzenesulfonamide was added to a mixture of 90 ml of water and 210 ml of concentrated sulfuric acid. This mixture was heated to 140°-145° C., allowed to cool slowly to room temperature, then cooled to −10° C., poured onto ice, made basic with 550 ml of concentrated ammonium hydroxide and cooled to 0° C. This mixture was extracted with dichloromethane. The extract was passed through hydrous magnesium silicate and washed with 200 ml of dichloromethane. The dichloromethane filtrate and wash was combined with 300 ml of hexane, concentrated to 300 ml, diluted to 800 ml with hexane, treated with charcoal, clarified and cooled to −10° C. This material was filtered, the filtrate concentrated to turbidity and cooled at −10° C. The precipitate was collected, washed with hexane and dried at 60° C. in vacuo, giving 2.3 g of the desired product, mp 142°-143° C.

EXAMPLE 167

[7-[3-(Ethylamino)phenyl]pyrazolo[1,5-a]pyrimidin-3-yl]phenylmethanone

A mixture of 6.2 g of 3-amino-1H-pyrazol-4-yl)-2-phenylmethanone and 12.4 g of N-[3-[3-(dimethylamino)-1-oxo-2-propenyl]phenyl]-N-ethyl-4-methylbenzenesulfonamide was reacted as described in Example 166, giving 1.4 g of the desired product, mp 98°-99° C.

EXAMPLE 168

N-[3-[3-(Dimethylamino)-1-oxo-2-propenyl]phenyl]acetamide

A 30.0 g portion of 3-acetamidoacetophenone was heated with 50 ml of dimethylformamide dimethylacetal on a steam bath under inert atmosphere for 8 hours. After cooling, the precipitated material was collected by filtration to yield the desired material as orange crystals (37.20 g, mp 184°-185° C.).

EXAMPLE 169

N-[3-[3-(Dimethylamino)-1-oxo-2-propenyl]phenyl]propanamide

In the manner of the above example, substituting 3-propanamidoacetophenone for 3-acetamidoacetophenone gave the desired product as pale orange crystals, mp 106°-108° C.

EXAMPLE 170

N-[3-[3-Dimethylamino)-1-oxo-2-propenyl]phenyl]butanamide

In the manner of Example 168, substituting 3-butanamidoacetophenone for 3-acetamidoacetophenone gave the desired compound as yellow-orange crystals, mp 113°-115° C.

EXAMPLE 171

N-[4-[3-(Dimethylamino)-1-oxo-2-propenyl]phenyl]acetamide

In the manner of Example 168, substituting 4-acetamidoacetophenone for 3-acetamidoacetophenone gave the desired compound as pale yellow crystals, mp 185°-186° C.

EXAMPLE 172

N-[4-[3-(Dimethylamino)-1-oxo-2-propenyl]phenyl]propanamide

In the manner of Example 168, substituting 4-propanamidoacetophenone for 3-acetamidoacetophenone gave the desired compound as yellow-orange crystals, mp 161°-163° C.

EXAMPLE 173

N-[3-[3-(Dimethylamino)-1-oxo-2-propenyl]phenyl]-N-methylacetamide

A solution of 4.62 g of N-[3-[3-(dimethylamino)-1-oxo-2-propenyl]phenyl]acetamide in 25 ml of dimethylformamide was stirred in an inert atmosphere and 1.0 g of sodium hydride (60% oil suspension) was added. After stirring for 1 hour, the liberation of hydrogen had ceased and a solution of 3.0 g of methyl iodide in 10 ml of dimethylformamide was gradually added (with cooling, if necessary). After stirring for an additional 1 hour at room temperature, any volatiles were removed at reduced pressure and then the reaction mixture was triturated 3 times with 100 ml of hexane. The reaction mixture was carefully poured into cold water and extracted exhaustively with methylene chloride. This material was evaporated at reduced pressure to yield a yellow-orange solid. A solution of the crude solid in methylene chloride was passed through a pad of hydrous magnesium silicate. Addition of hexane to the refluxing eluate gave crystals which were collected after cooling. The desired compound was a yellow-orange crystalline material, mp 146°-148° C.

EXAMPLE 174

N-[3-[3-(Dimethylamino)-1-oxo-2-propenyl]phenyl]-N-ethylacetamide

In the manner of Example 173 substituting ethyl iodide for methyl iodide and following the procedure outlined above, the desired compound was isolated as yellow-orange crystals, mp 110°-113° C.

EXAMPLE 175

N-[3-[3-(Dimethylamino)-1-oxo-2-propenyl]phenyl]-N-methylpropanamide

In the manner of Example 173, substituting N-[3-[3-(dimethylamino)-1-oxo-2-propenyl]phenyl]propanamide for N-[3-[3-(dimethylamino)-1-oxo-2-propenyl]phenyl]acetamide and following the procedure outlined in Example 173, the desired product was isolated as a pale yellow crystalline solid, mp 148°-149° C.

EXAMPLE 176

N-[3-[3-(Dimethylamino)-1-oxo-2-propenyl]phenyl]-N-ethylpropanamide

In the manner of Example 175, substituting ethyl iodide for methyl iodide and following the exact procedure in Example 173, the desired material was isolated as a yellow crystalline solid, mp 105°-107° C.

EXAMPLE 177

N-[4-[3-(Dimethylamino)-1-oxo-2-propenyl]phenyl]-N-methylpropanamide

A soluton of 3.10 g of N-[4-[3-(dimethylamino)-1-oxo-2-propenyl]phenyl]propanamide in 25 ml dimethylformamide was stirred in an inert atmosphere and 0.60 g of sodium hydride (60% oil suspension) was added. After stirring for 1 hour, the liberation of hydrogen had ceased and a solution of 1.8 g of methyl iodide in 5 ml of dimethylformamide was added portionwise. After stirring for an additional hour, the system was evaporated to remove volatiles and then the reaction mixture was triturated 3 times with hexane (3×50 ml). The reaction mixture was carefully poured into cold water and extracted with methylene chloride. The methylene chloride solution was dried and evaporated to dryness at reduced pressure to yield a crystalline solid. Recrystallization from methylene chloridehexane gave a yellow crystalline solid, mp 76°-78° C.

EXAMPLE 178

N-[4-[3-(Dimethylamino)-1-oxo-2-propenyl]phenyl]-N-ethylpropanamide

In the manner of Example 177, substituting ethyl iodide for methyl iodide and following the procedure outlined in that example, the desired compound was isolated as a low melting yellow-orange crystalline compound, mp 75°-77° C.

EXAMPLE 179

N-[3-(3-Benzylpyrazolo[1,5-a]pyrimidin-7-yl)phenyl]acetamide

A solution of 1.87 g of 3-amino-4-benzoylpyrazole and 2.32 g of N-[3-[3-(dimethylamino)-1-oxo-2-propenyl]phenyl]acetamide (Example 168) in 50 ml of glacial acetic acid was refluxed for 8 hours. The reaction mixture was evaporated to dryness and a saturated sodium bicarbonate solution was added along with 400 ml of methylene chloride. The solid that separated was recovered by filtration and was the desired compound (2.57 g, mp 205°-207° C.). The methylene chloride solution afforded more compound (0.73 g, mp 205°-207° C.).

EXAMPLE 180

N-[3-(3-Benzoylpyrazolo[1,5-a]pyrimidin-7-yl)phenyl]-N-methylacetamide

In the manner of Example 179, substituting N-[3-[3-(dimethylamino)-1-oxo-2-propenyl]phenyl]-N-methylacetamide (Example 171) for N-[3-[3-(dimethylamino)-1-oxo-2-propenyl]phenyl]acetamide gave the desired product, mp 162°-164° C.

EXAMPLE 181

N-[3-(3-Benzoylpyrazolo[1,5-a]pyrimidin-7-yl)phenyl]-N-ethylacetamide

In the manner of Example 179, substituting N-[3-[3-(dimethylamino)-1-oxo-2-propenyl]phenyl]-N-ethylacetamide (Example 174) for N-[3-[3-(dimethylamino)-1-oxo-2-propenyl]phenyl]acetamide gave the product of the example, mp 158°-160° C.

EXAMPLE 182

N-[3-[3-(2-Furancarbonyl)pyrazolo[1,5-a]pyrimidin-7-yl]phenyl]acetamide

A solution of 1.77 g of 3-amino-4-furanylpyrazole and 2.32 g of N-[3-[3-(dimethylamino)-1-oxo-2-propenyl]phenyl]acetamide (Example 168) in 50 ml of glacial acetic acid was refluxed for 10 hours. Evaporation of the reaction mixture gave a solid which was treated with a saturated sodium bicarbonate solution and 200 ml of methylene chloride. The solid that precipitated was recovered by filtration and proved to be the desired product (2.57 g, mp 195°-196° C.). An additional quantity of product was isolated from the methylene chloride solution, mp 195°-196° C.

EXAMPLE 183

N-[3-[3-(2-Furancarbonyl)pyrazolo[1,5-a]pyrimidin-7-yl]phenyl]-N-methylacetamide In the manner of the above example, substituting N-[3-[3-(dimethylamino)-1-oxo-2-propenyl]phenyl]-N-methylacetamide (Example 171) for N-[3-[3-(dimethylamino)-1-oxo-2-propenyl]phenyl]acetamide gave the desired product, mp 210°-212° C., which was isolated from the methylene chloride solution.

EXAMPLE 184

N-Ethyl-N-[3-[3-(2-furanylcarbonyl)pyrazolo[1,5-a]pyrimidin-7-yl]acetamide

In the manner of Example 182, substituting N-[3-[3-(dimethylamino)-1-oxo-2-propenyl]phenyl]-N-ethylacetamide (Example 174) for N-[3-[3-(dimethylamino)-1-oxo-2-propenyl]phenyl]acetamide gave the desired product isolated from the methylene chloride extract, mp 194°–196° C.

EXAMPLE 185

N-[3-(3-Benzoylpyrazolo[1,5-a]pyrimidin-7-yl)phenyl]propanamide

A solution of 1.87 g of 3-amino-4-benzoylpyrazole and 2.46 g of N-[3-[3-(dimethylamino)-1-oxo-2-propenyl]phenyl]propanamide (Example 169) in 50 ml of glacial acetic acid was refluxed for 15 hours and then evaporated to yield a pale yellow gum. This material was partitioned between an aqueous saturated sodium bicarbonate solution and methylene chloride. The methylene chloride solution was dried with powdered anhydrous sodium sulfate and then passed through a short column of hydrous magnesium silicate adsorbent. The eluate was refluxed in a steam bath and hexane gradually added until turbidity. After cooling, the desired product was recovered by filtration (2.39 g, mp 172°–174° C.).

EXAMPLE 186

N-[3-(3-Benzoylpyrazolo[1,5-a]pyrimidin-7-yl)phenyl]-N-methylpropanamide

In the manner of the above example substituting N-[3-[3-(dimethylamino)-1-oxo-2-propenyl]phenyl]-N-methylpropanamide (Example 175) for N-[3-[3-(dimethylamino)-1-oxo-2-propenyl]phenyl]propanamide gave the desired compound, mp 154°–156° C.

EXAMPLE 187

N-[3-(3-Benzoylpyrazolo[1,5-a]pyrimidin-7-yl)phenyl]N-ethylpropanamide

In the manner of Example 185, substituting N-[3-[3-(dimethylamino)-1-oxo-2-propenyl]phenyl]-N-ethylpropanamide for N-[3-[3-(dimethylamino)-1-oxo-2-propenyl]phenyl]propanamide gave the desired compound, mp 194°–195° C.

EXAMPLE 188

N-[3-[3-(2-Furanylcarbonyl)pyrazolo[1,5-a]pyrimidin-7-yl]phenyl]propanamide

A solution of 1.77 g 3-amino-4-furanylpyrazole and 2.46 g of N-[3-[3-(dimethylamino)-1-oxo-2-propenyl]phenyl]propanamide in 50 ml of glacial acetic acid was refluxed for 8 hours. Removal of all solvents gave a gum which was partitioned between an aqueous saturated sodium bicarbonate solution and methylene chloride. The methylene chloride extract was dried with powdered anhydrous sodium sulfate and then passed through a short column of a hydrous magnesium silicate adsorbent. The eluate was refluxed on a steam bath with gradual addition of hexanes until turbidity was noted. The desired product was collected by filtration of the cooled crystallization mixture, (2.05 g, mp 185°–186° C.).

EXAMPLE 189

N-[3-[3-(2-Furanylcarbonyl)pyrazolo[1,5-a]pyrimidin-7-yl]phenyl]-N-methylpropanamide In the manner of the above example, substituting N-[3-[3-(dimethylamino)-1-oxo-2-propenyl]phenyl]-N-methylpropanamide for N-[3-[3-(dimethylamino)-1-oxo-2-propenyl]phenyl]propanamide gave the desired product, mp 153°–155° C.

EXAMPLE 190

N-Ethyl-N-[3-[3-(2-furanylcarbonyl)pyrazolo[1,5-a]pyrimidin-7-yl]phenyl]propanamide In the manner of Example 188, substituting N-[3-[3-(dimethylamino)-1-oxo-2-propenyl]phenyl]-N-ethylpropanamide (Example 176) for N-[3-[3-(dimethylamino)-1-oxo-2-propenyl]phenyl]propanamide gave the desired compound, mp 165°–167° C.

EXAMPLE 191

N-[4-(3-Benzoylpyrazolo[1,5-a]pyrimidin-7-yl)phenyl]acetamide

In the manner of Example 179, substituting N-[4-[3-(dimethylamino)-1-oxo-2-propenyl]phenyl]acetamide for N-[3-[3-(dimethylamino)-1-oxo-2-propenyl]phenyl]acetamide gave the desired compound, mp 229°–231° C.

EXAMPLE 192

N-[4-(3-Benzoylpyrazole[1,5-a]pyrimidin-7-yl)phenyl]-N-methylacetamide

In the manner of Example 179, substituting N-[4-[3-(dimethylamino)-1-oxo-2-propenyl]phenyl]-N-methylacetamide for N-[3-[3-(dimethylamino)-1-oxo-2-propenyl]phenyl]acetamide gave the desired product, mp 173°–175° C.

EXAMPLE 193

N-[4-[3-(2-Furanylcarbonyl)pyrazolo[1,5-a]pyrimidin-7-yl]phenyl]-N-methylacetamide A solution of 1.77 g of 3-amino-4-furanylpyrazole and 2.46 g of N-[4-[3-(dimethylamino)-1-oxo-2-propenyl]phenyl]-N-methylacetamide in 50 ml of glacial acetic acid was refluxed for 8 hours. Evaporation of the reaction mixture gave a gum which was partitioned between an aqueous saturated sodium bicarbonate solution and methylene chloride. The methylene chloride extract was dried and passed through a short column of hydrous magnesium silicate adsorbent. The eluate was refluxed on a steam bath with gradual addition of hexane until turbidity. On cooling, the desired compound was collected by filtration, mp 202°–204° C.

EXAMPLE 194

N-[4-(3-Benzoylpyrazolo[1,5-a]pyrimidin-7-yl)phenyl]propanamide

In the manner of Example 179, substituting N-[4-[3-(dimethylamino)-1-oxo-2-propenyl]phenyl]propanamide for N-[3-[3-(dimethylamino)-1-oxo-2-propenyl]phenyl]acetamide gave the desired product, mp 211°–213° C.

EXAMPLE 195

N-[4-[3-(2-Furanylcarbonyl)pyrazolo[1,5-a]pyrimidin-7-yl]phenyl]propanamide

In the manner of Example 188, substituting N-[4-[3-(dimethylamino)-1-oxo-2-propenyl]phenyl]propanamide for N-[3-[3-(dimethylamino)-1-oxo-2-propenyl]phenyl]propanamide gave the desired product, mp 235°–237° C.

EXAMPLE 196

[5-Methyl-7-(2-thienyl)pyrazolo[1,5-a]pyrimidin-3-yl]phenyl-methanone

A mixture of 0.01 mole of 1-(2-thienyl)butan-1,3-dione was reacted with pyrrolidine in ethyl acetate to give 3-(1-pyrrolidinyl)-1-(2-thienyl)-2-buten-1-one, mp 154°–156° C.

The title compound may then be prepared as follows:

A 0.10 mole portion of the above compound and 0.10 mole of (3-amino-1H-pyrazol-4-yl)phenyl-methanone in 75 ml of glacial acetic acid is refluxed for 6 hours. The solvent is removed and the product isolated as described in Example 1.

We claim:

1. A compound selected from those of the formula:

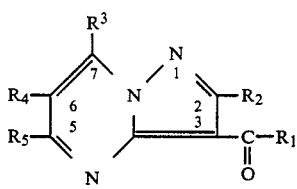

wherein $R_1$ is selected from the group consisting of unsubstituted phenyl; phenyl mono- or di-substituted by halogen, alkoxy($C_1$–$C_3$) or alkyl($C_1$–$C_3$); phenyl mono-substituted by trifluoromethyl, alkylthio($C_1$–$C_3$), alkylamino($C_1$–$C_3$), dialkylamino($C_1$–$C_3$), methylenedioxy, alkylsulfonyl($C_1$–$C_3$) or alkanoylamino($C_1$–$C_3$); naphthalenyl; thiazolyl; biphenyl; thienyl; furanyl; pyridinyl; substituted thiazolyl; substituted biphenyl; substituted thienyl; and substituted pyridinyl wherein the substituents are selected from one or two of the group consisting of halogen, alkoxy($C_1$–$C_3$) and alkyl($C_1$–$C_3$); $R_2$, $R_4$ and $R_5$ are each selected from the group consisting of hydrogen and alkyl($C_1$–$C_3$); and $R_3$ is selected from the group consisting of unsubstituted phenyl, phenyl mono-substituted by halogen, trifluoromethyl, alkoxy($C_1$–$C_3$), amino, alkyl($C_1$–$C_3$), alkylamino($C_1$–$C_6$), dialkylamino($C_1$–$C_3$), alkanoylamino($C_1$–$C_6$), N-alkyl($C_1$–$C_6$)alkanoylamino($C_1$–$C_6$), cyano or alkylthio($C_1$–$C_3$); furanyl; thienyl; pyridinyl; and pyridine-1-oxide.

2. A compound according to claim 1, wherein $R_1$ is 2-furanyl; $R_2$, $R_4$ and $R_5$ are each hydrogen; and $R_3$ is selected from the group consisting of 3-(trifluoromethyl)phenyl; 3-pyridinyl; and 4-pyridinyl.

3. A compound according to claim 1, wherein $R_1$ is selected from the group consisting of unsubstituted phenyl; phenyl substituted by 4-methyl, 4-ethyl, 4-methoxy, 3,4-dimethoxy or 4-dimethylamino; 2-furanyl; 2-thienyl; 2-pyridinyl; and 4-pyridinyl; $R_2$, $R_4$ and $R_5$ are each hydrogen; and $R_3$ is selected from the group consisting of 3-(trifluoromethyl)phenyl; 3-pyridinyl; 4-pyridinyl; 3-[N-alkyl($C_1$–$C_6$)alkanoylamino($C_1$–$C_6$)]phenyl; and 3-[alkylamino($C_1$–$C_6$)].

4. The compound according to claim 1, phenyl[7-(3-pyridinyl)pyrazolo[1,5-a]pyrimidin-3-yl]methanone.

5. The compound according to claim 1, (4-fluorophenyl)[7-(4-pyridinyl)pyrazolo[1,5-a]pyrimidin-3-yl]methanone.

6. The compound according to claim 1, phenyl[7-(4-pyridinyl)pyrazolo[1,5-a]pyrimidin-3-yl]methanone.

7. The compound according to claim 1, phenyl[7-[3-(trifluoromethyl)phenyl]pyrazolo[1,5-a]pyrimidin-3-yl]methanone.

8. The compound according to claim 1, (4-methoxyphenyl)[7-(3-pyridinyl)pyrazolo[1,5-a]pyrimidin-3-yl]methanone.

9. The compound according to claim 1, (3-fluorophenyl)[7-(4-pyridinyl)pyrazolo[1,5-a]pyrimidin-3-yl]methanone.

10. The compound according to claim 1, [7-(3-pyridinyl)pyrazolo[1,5-a]pyrimidin-3-yl][3-(trifluoromethyl)phenyl]methanone.

11. The compound according to claim 1, 2-thienyl[7-[3-(trifluoromethyl)phenyl]pyrazolo[1,5-a]pyrimidin-3-yl]methanone.

12. The compound according to claim 1, 2-furanyl[7-[3-(trifluoromethyl)phenyl]pyrazolo[1,5-a]pyrimidin-3-yl]methanone.

13. The compound according to claim 1, 2-furanyl[7-(3-pyridinyl)pyrazolo[1,5-a]pyrimidin-3-yl]methanone.

14. The compound according to claim 1, [2-methyl-7-(3-pyridinyl)pyrazolo[1,5-a]pyrimidin-3-yl]phenylmethanone.

15. The compound according to claim 1, (4-methylphenyl)[7-(3-pyridinyl)pyrazolo[1,5-a]pyrimidin-3-yl]methanone.

16. The compound according to claim 1, phenyl[7-(4-pyridinyl)pyrazolo[1,5-a]pyrimidin-3-yl]methanone, pyridine-1-oxide.

17. The compound according to claim 1, 2-pyridinyl[7-(3-pyridinyl)pyrazolo[1,5-a]pyrimidin-3-yl]methanone.

18. The compound according to claim 1, 2-pyridinyl[7-[3-(trifluoromethyl)phenyl]pyrazolo[1,5-a]pyrimidin-3-yl]methanone.

19. The compound according to claim 1, 2-pyridinyl[7-(4-pyridinyl)pyrazolo[1,5-a]pyrimidin-3-yl]methanone.

20. The compound according to claim 1, [7-(3-pyridinyl)pyrazolo[1,5-a]pyrimidin-3-yl]-2-thiazolylmethanone.

21. The compound according to claim 1, 4-pyridinyl[7-(3-pyridinyl)pyrazolo[1,5-a]pyrimidin-3-yl]methanone.

22. The compound according to claim 1, 4-pyridinyl[7-[3-(trifluoromethyl)phenyl]pyrazolo[1,5-a]pyrimidin-3-yl]methanone.

23. The compound according to claim 1, (2-fluorophenyl)[7-(3-pyridinyl)pyrazolo[1,5-a]pyrimidin-3-yl]methanone.

24. The compound according to claim 1, (2-fluorophenyl)[7-[3-(trifluoromethyl)phenyl]pyrazolo[1,5-a]pyrimidin-3-yl]methanone.

25. The compound according to claim 1, [7-[3-(ethylamino)phenyl]pyrazolo[1,5-a]pyrimidin-3-yl]-2-furanylmethanone.

26. The compound according to claim 1, [7-[3-(ethylamino)phenyl]pyrazolo[1,5-a]pyrimidin-3-yl]phenylmethanone.

27. A method of meliorating anxiety in a mammal suffering from anxiety which comprises administering to said mammal an effective anxiolytic amount of a compound of claim 1.

28. A method of treating epilepsy in a mammal suffering from epilepsy which comprises administering to said mammal an effective anticonvulsant amount of a compound of claim 1.

29. A method of inducing sedation or hypnosis in a mammal which comprises administering to said mammal an effective sedative or hypnotic amount of a compound of claim 1.

30. A method of inducing skeletal muscle relaxation in a mammal which comprises administering to said mammal an effective skeletal muscle relaxant amount of a compound of claim 1.

31. A composition of matter in dosage unit form comprising from 2-750 mg of a compound of claim 1 in association with a pharmaceutically acceptable carrier.

* * * * *